United States Patent
Tsuneoka et al.

(10) Patent No.: US 7,335,747 B2
(45) Date of Patent: Feb. 26, 2008

(54) CANCER ASSOCIATED GENE MINA 53, PROTEIN MINA 53 AND MONOCLONAL ANTIBODY THEREOF

(75) Inventors: Makoto Tsuneoka, Kurume (JP); Hiroshi Kimura, Kurume (JP)

(73) Assignee: Gakkouhoujin Kurume University, Fukuoka (JP)

(*) Notice: Subject to any disclaimer, the term of this patent is extended or adjusted under 35 U.S.C. 154(b) by 228 days.

(21) Appl. No.: 10/509,073

(22) PCT Filed: Apr. 14, 2003

(86) PCT No.: PCT/JP03/04699

§ 371 (c)(1),
(2), (4) Date: Jan. 12, 2005

(87) PCT Pub. No.: WO03/087363

PCT Pub. Date: Oct. 23, 2003

(65) Prior Publication Data

US 2006/0234318 A1    Oct. 19, 2006

(30) Foreign Application Priority Data

Apr. 12, 2002  (JP) ............................. 2002-111377

(51) Int. Cl.
*C07K 16/00* (2006.01)
*C12P 21/08* (2006.01)

(52) U.S. Cl. .................. 530/388.1; 435/326; 435/330; 530/387.7; 530/388.85

(58) Field of Classification Search .................. None
See application file for complete search history.

(56) References Cited

U.S. PATENT DOCUMENTS 5,547,928 A * 8/1996 Wu et al. .................. 514/2

FOREIGN PATENT DOCUMENTS

| EP | 1074617 A2 * | 7/2000 |
| EP | 1 074 617 | 2/2001 |
| EP | 1074617 A2 * | 2/2001 |

OTHER PUBLICATIONS

Campbell, A.M., Monoclonal antibody technology. 1984. Chapter 1, pp. 1-32.*
Skolnick, J., and Fetrow, J.S. From genes to protein structure and function: novel applications of computational approaches in the genomic era. 2000. Trends in Biotechnology, vol. 18 No. 1, pp. 34-39.*
Sigma catalog (Life Science Research Immunochemicals)1998. pp. 3 and 198.*
M. Tsuneoka et al., "A Novel Myc Target Gene, Mina 53, that is Involved in Cell Proliferation", J. Biol. Chem., Sep. 20, 2002, vol. 277, No. 38, pp. 35450-35459.
A. Semov et al., "Microarray Analysis of E-Box Binding-Related Gene Expression in Young and Replicatively Senescent Human Fibroblasts", Anal. Biochem., Mar. 1, 2002, vol. 302, No. 1, pp. 38-51.
M. Tsuneoka et al., "Mina53 as a Potential Prognostic Factor for Esophageal Squamous Cell Carcinoma", Clinical Cancer Research, Nov. 1, 2004, vol. 10, pp. 7347-7356.
K. Teye et al.,"Increased Expression of a Myc Target Gene Mina53 in Human Colon Cancer", American Journal of Pathology, Jan. 2004, vol. 164, No. 1, pp. 205-216.
Genbank Accession No. AX875833, 2003.
C. V. Dang, "c-Myc Target Genes Involved in Cell Growth, Apoptosis, and Metabolism", Molecular and Cellular Biology, vol. 19, No. 1, pp. 1-11, Jan. 1999.
Database EMBL, Oct. 8, 2001, "*Homo sapiens* MYC induced nuclear antigen, transcript variant 2, mRNA, complete cds.", XP002362927, Database Accession No. BC014928.
Database EMBL, May 15, 2001, "*Homo sapiens* cDNA FLJ14393 fis, clone HEMBA1003222.", XP002362928, Data Accession No. AK027299.

* cited by examiner

*Primary Examiner*—Larry R. Helms
*Assistant Examiner*—Anne M. Gussow
(74) *Attorney, Agent, or Firm*—Wenderoth, Lind & Ponack, L.L.P.

(57) ABSTRACT

Myc protein is an unevenly distributed intermediate agent for cell proliferation, and activates a gene expression via E.box. Mina53 gene encodes a protein of 53 kDa molecular weight and is present in the nucleoplasm and nucleolus. Mina53 mRNA and protein expression are induced by artificial introduction of c-Myc activity. E.box site is present in the vicinity of the transcription initiation site of mina53 gene, and the expression from mina53 promoter is activated by c-Myc through the medium of E.box. Specific inhibition of mina53 expression in HeLa cells and rat fibroblast cells 3Y1 having high expression c.myc strikingly inhibits cell proliferation. The combination of these results show that mina53 is a Myc target gene and is associated with cell proliferation in mammals.

5 Claims, 17 Drawing Sheets

A, Relationship between Mina53 and Accumulated Survival Rate of Esophageal Cancer B, Relationship between Ki-67 and Accumulated Survival Rate of Esophageal Cancer

SEQUENCE LISTING

<160> NUMBER OF SEQ ID NOS: 3

<210> SEQ ID NO 1
<211> LENGTH: 1395
<212> TYPE: DNA
<213> ORGANISM: Homo sapiens

<400> SEQUENCE: 1

```
atg cca aag aaa gca aag cct aca ggg agt ggg aag gaa gag ggg ccg      48
Met Pro Lys Lys Ala Lys Pro Thr Gly Ser Gly Lys Glu Glu Gly Pro
                 5                  10                  15 gct ccc tgt aag cag atg aag tta gaa gca gct ggg ggg cct tca gct      96
Ala Pro Cys Lys Gln Met Lys leu Glu Ala Ala Gly Gly Pro Ser Ala
             20                  25                  30 tta aac ttt gac agt ccc agt agt ctc ttt gaa agt tta atc tcg ccc     144
Leu Asn Phe Asp Ser Pro Ser Ser Leu Phe Glu Ser Leu Ile Ser Pro
         35                  40                  45 atc aag aca gag act ttt ttc aag gaa ttc tgg gag cag aag ccc ctt     192
Ile Lys Thr Glu Thr Phe Phe Lys Glu Phe Trp Glu Gln Lys Pro Leu
     50                  55                  60 ctc att cag aga gat gac cct gca ctg gcc aca tac tat ggg tcc ctg     240
Leu Ile Gln Arg Asp Asp Pro Ala Leu Ala Thr Tyr Tyr Gly Ser Leu
 65                  70                  75                  80 ttc aag cta aca gat ctg aag agt ctg tgc agc cgg ggg atg tac tat     288
Phe Lys Leu Thr Asp Leu Lys Ser Leu Cys Ser Arg Gly Met Tyr Tyr
                 85                  90                  95 gga aga gat gtg aat gtc tgc cgg tgt gtc aat ggg aag aag aag gtt     336
Gly Arg Asp Val Asn Val Cys Arg Cys Val Asn Gly Lys Lys Lys Val
            100                 105                 110 tta aat aaa gat ggc aaa gca cac ttt ctt cag ctg aga aaa gat ttt     384
Leu Asn Lys Asp Gly Lys Ala His Phe Leu Gln Leu Arg Lys Asp Phe
        115                 120                 125 gat cag aaa agg gca acg att cag ttt cac caa cct cag aga ttt aag     432
Asp Gln Lys Arg Ala Thr Ile Gln Phe His Gln Pro Gln Arg Phe Lys
    130                 135                 140 gat gag ctt tgg agg atc cag gag aag ctg gaa tgt tac ttt ggc tcc     480
Asp Glu Leu Trp Arg Ile Gln Glu Lys Leu Glu Cys Tyr Phe Gly Ser
145                 150                 155                 160 ttg gtt ggc tcg aat gtg tac ata act ccc gca gga tct cag ggc ctg     528
Leu Val Gly Ser Asn Val Tyr Ile Thr Pro Ala Gly Ser Gln Gly Leu
                165                 170                 175 ccg ccc cat tat gat gat gtc gag gtt ttc atc ctg cag ctg gag gga     576
Pro Pro His Tyr Asp Asp Val Glu Val Phe Ile Leu Gln Leu Glu Gly
            180                 185                 190 gag aaa cac tgg cgc ctc tac cac ccc act gtg ccc ctg gca cga gag     624
Glu Lys His Trp Arg Leu Tyr His Pro Thr Val Pro Leu Ala Arg Glu
```

-continued

```
              195                 200                 205
tac agc gtg gag gcc gag gaa agg atc ggc agg ccg gtg cat gag ttt      672
Tyr Ser Val Glu Ala Glu Glu Arg Ile Gly Arg Pro Val His Glu Phe
    210                 215                 220 atg ctg aag ccg ggt gat ttg ttg tac ttt ccc aga gga acc att cat      720
Met Leu Lys Pro Gly Asp Leu Leu Tyr Phe Pro Arg Gly Thr Ile His
225                 230                 235                 240 caa gcg gac act cct gcg ggg ctg gcc cac tcg act cac gtg acc atc      768
Glu Ala Asp Thr Pro Ala Gly Leu Ala His Ser Thr His Val Thr Ile
                245                 250                 255 agc acc tac cag aac aat tca tgg gga gat ttc ctt ttg gat acc atc      816
Ser Thr Tyr Gln Asn Asn Ser Trp Gly Asp Phe Leu Leu Asp Thr Ile
            260                 265                 270 tcg ggg ctt gta ttt gat act gca aag gaa gac gtg gag tta cgg acc      864
Ser Gly Leu Val Phe Asp Thr Ala Lys Glu Asp Val Glu Leu Arg Thr
        275                 280                 285 ggc ata ccc cgg cag ctg ctc ctg gtg gaa tcc aca act gtt gct aca      912
Gly Ile Pro Arg Gln Leu Leu Leu Val Glu Ser Thr Thr Val Ala Thr
    290                 295                 300 aga cga tta agt ggc ttc ctg agg aca ctt gca gac cgg ctg gag ggc      960
Arg Arg Leu Ser Gly Phe Leu Arg Thr Leu Ala Asp Arg Leu Glu Gly
305                 310                 315                 320 acc aaa gaa ctg ctt tcc tca gac atg aag aag gat ttt att atg cac     1008
Thr Lys Glu Leu Leu Ser Ser Asp Met Lys Lys Asp Phe Ile Met His
                325                 330                 335 aga ctc ccc cct tac tct gcg gga gat ggg gca gag ctg tca aca cca     1056
Arg Leu Pro Pro Tyr Ser Ala Gly Asp Gly Ala Glu Leu Ser Thr Pro
            340                 345                 350 ggt gga aag tta ccg agg ctg gac agt gta gtg aga ctg cag ttt aaa     1104
Gly Gly Lys Leu Pro Arg Leu Asp Ser Val Val Arg Leu gln Phe Lys
        355                 360                 365 gac cac att gtc ctc aca gta ctg ccg gat caa gat caa tct gat gaa     1152
Asp His Ile Val Leu Thr Val Leu Pro Asp Gln Asp Gln Ser Asp Glu
    370                 375                 380 gct caa gaa aag atg gtg tac atc tat cat tcc tta aag aat agt aga     1200
Ala Gln Glu Lys Met Val Tyr Ile Tyr His Ser Leu Lys Asn Ser Arg
385                 390                 395                 400 gag aca cac atg atg gga aat gag gag gaa aca gag ttt cat gga ctt     1248
Glu Thr His Met Met Gly Asn Glu Glu Glu Thr Glu Phe His Gly Leu
                405                 410                 415 cgc ttc cct ttg tca cat ttg gat gca ctg aag caa att tgg aat agt     1296
Arg Phe Pro Leu Ser His Leu Asp Ala Leu Lys Gln Ile Trp Asn Ser
            420                 425                 430 cca gct att tct gtc aag gac ctg aaa ctt act aca gat gag gaa aag     1344
Pro Ala Ile Ser Val Lys Asp Leu Lys Leu Thr Thr Asp Glu Glu Lys
        435                 440                 445 gaa agc ctg gta tta tcc ctc tgg aca gaa tgt tta att caa gta gtc     1392
Glu Ser Leu Val Leu Ser Leu Trp Thr Glu Cys Leu Ile Gln Val Val
    450                 455                 460 tag                                                                 1395

<210> SEQ ID NO 2
<211> LENGTH: 1398
<212> TYPE: DNA
<213> ORGANISM: Mus musculus

<400> SEQUENCE: 2 atg cca aag aaa gtg cag ccc aca ggg gat gag aac gaa gaa gag tct       48
Met Pro Lys Lys Val Gln Pro Thr Gly Asp Glu Asn Glu Glu Glu Ser
                 5                  10                  15
```

-continued

| | |
|---|---|
| gtt cct tgc aag cgg gtg aag gag gag ctg cct gaa acg ctt tct gta<br>Val Pro Cys Lys Arg Val Lys Glu Glu Leu Pro Glu Thr Leu Ser Val<br>20                         25                   30 | 96 |
| tta aac ttt gac agc ccc agt agt ttc ttc gaa agt tta atc tca ccc<br>Leu Asn Phe Asp Ser Pro Ser Ser Phe Phe Glu Ser Leu Ile Ser Pro<br>35                       40                   45 | 144 |
| atc aaa gta gag act ttt ttc aag gaa ttc tgg gaa caa aag ccc ctt<br>Ile Lys Val Glu Thr Phe Phe Lys Glu Phe Trp Glu Gln Lys Pro Leu<br>50                       55                  60 | 192 |
| ctc att cag agg gat gac cct gta ctg gcc aaa tat tac cag tct ctg<br>Leu Ile Gln Arg Asp Asp Pro Val Leu Ala Lys Tyr Tyr Gln Ser Leu<br>65                       70                  75                  80 | 240 |
| ttc agc ctc tca gat ctg aag aga ctc tgc aag aaa gga gtg tac tat<br>Phe Ser Leu Ser Asp Leu Lys Arg Leu Cys Lys Lys Gly Val Tyr Tyr<br>                     85                  90                   95 | 288 |
| gga aga gac gtg aat gtc tgc cgg agc atc agt ggg aag aag aag gtt<br>Gly Arg Asp Val Asn Val Cys Arg Ser Ile Ser Gly Lys Lys Lys Val<br>                    100               105               110 | 336 |
| tta aat aag gat ggc aga gca cat ttt ctt cag ctg aga aaa gat ttt<br>Leu Asn Lys Asp Gly Arg Ala His Phe Leu Gln Leu Arg Lys Asp Phe<br>115                   120               125 | 384 |
| gat cag aag agg gca aca att cag ttt cac caa cct cag aga tat aag<br>Asp Gln Lys Arg Ala Thr Ile Gln Phe His Gln Pro Gln Arg Tyr Lys<br>130                   135               140 | 432 |
| gat gag ctg tgg cgg atc cag gaa aag ctg gaa tgt tac ttt ggg tcc<br>Asp Glu Leu Trp Arg Ile Gln Glu Lys Leu Glu Cys Tyr Phe Gly Ser<br>145                   150               155               160 | 480 |
| tta gta ggc tcg aat gtg tac atg act cct gca gga tct cag ggc ctc<br>Leu Val Gly Ser Asn Val Tyr Met Thr Pro Ala Gly Ser Gln Gly Leu<br>                    165               170               175 | 528 |
| cct cca cat tat gat gat gtt gag gtt ttt atc ctg cag ctg gag gga<br>Pro Pro His Tyr Asp Asp Val Glu Val Phe Ile Leu Gln Leu Glu Gly<br>                    180               185               190 | 576 |
| acg aaa cac tgg cgc ctg tac tcc cca act gtg ccc ctg gca cac gag<br>Thr Lys His Trp Arg Leu Tyr Ser Pro Thr Val Pro Leu Ala His Glu<br>                    195               200               205 | 624 |
| tac agt gtg gaa tct gag gac cgg atc ggc aca ccg aca cac gac ttc<br>Tyr Ser Val Glu Ser Glu Asp Arg Ile Gly Thr Pro Thr His Asp Phe<br>210                   215               220 | 672 |
| ctg ctg aag cct gga gat ttg ttg tac ttt ccc aga ggg acc att cat<br>Leu Leu Lys Pro Gly Asp Leu Leu Tyr Phe Pro Arg Gly Thr Ile His<br>225                   230               235               240 | 720 |
| cag gca gaa act cct tca ggc ctg gcc tac tct att cac ctg act att<br>Gln Ala Glu Thr Pro Ser Gly Leu Ala Tyr Ser Ile His Leu Thr Ile<br>                    245               250               255 | 768 |
| agc acc tac cag aac aat tca tgg gga gac tgc ctt ttg gat tcc att<br>Ser Thr Tyr Gln Asn Asn Ser Trp Gly Asp Cys Leu Leu Asp Ser Ile<br>                    260               265               270 | 816 |
| tcg ggg ttc gta ttt gac att gca aag gaa gat gtg gca tta agg agt<br>Ser Gly Phe Val Phe Asp Ile Ala Lys Glu Asp Val Ala Leu Arg Ser<br>275                   280               285 | 864 |
| gga atg ccc cgg cgg atg ctc ctg aat gtg gaa acc cca gct gat gta<br>Gly Met Pro Arg Arg Met Leu Leu Asn Val Glu Thr Pro Ala Asp Val<br>290                   295               300 | 912 |
| aca agg aag ttg agt ggc ttt ctg agg act ctt gca gac cag ctc gag<br>Thr Arg Lys Leu Ser Gly Phe Leu Arg Thr Leu Ala Asp Gln Leu Glu<br>305                   310               315               320 | 960 |
| ggc aga gaa gag ctg ctg tca tca gat atg aag aag gac ttc gtc aag<br>Gly Arg Glu Glu Leu Leu Ser Ser Asp Met Lys Lys Asp Phe Val Lys | 1008 |

-continued

```
                    325                 330                 335
cac aga ctc cct cct ttc ttc gag gga aat gga acg gag acg atg gac          1056
His Arg Leu Pro Pro Phe Phe Glu Gly Asn Gly Thr Glu Thr Met Asp
            340                 345                 350 cca ggt aaa cag ttg cca agg ttg gac aac ata ata aga ctg cag ttc          1104
Pro Gly Lys Gln Leu Pro Arg Leu Asp Asn Ile Ile Arg Leu Gln Phe
        355                 360                 365 aaa gat cac att gtc ctc aca gta ggg cca gat aag aat cca ttt gat          1152
Lys Asp His Ile Val Leu Thr Val Gly Pro Asp Lys Asn Pro Phe Asp
    370                 375                 380 gaa gct caa caa aag gtg gtt tac atc tat cat tct ctg aag aat gtg          1200
Glu Ala Gln Gln Lys Val Val Tyr Ile Tyr His Ser Leu Lys Asn Val
385                 390                 395                 400 agg cag atg cac atg ata gga gaa gag gag gaa tcc gag att ttc ggt          1248
Arg Gln Met His Met Ile Gly Glu Glu Glu Glu Ser Glu Ile Phe Gly
                405                 410                 415 ctt cgc ttt cct tta tca cat gtg gat gct ctg aag caa atc tgg tgc          1296
Leu Arg Phe Pro Leu Ser His Val Asp Ala Leu Lys Gln Ile Trp Cys
            420                 425                 430 ggg tca cca att cgt gtt aag gaa ctg aaa ctt gac aca gat gaa gaa          1344
Gly Ser Pro Ile Arg Val Lys Glu Leu Lys Leu Asp Thr Asp Glu Glu
        435                 440                 445 aag gag aac ctg gca ctg tct ctc tgg tcg gag tct tta atc caa gta          1392
Lys Glu Asn Leu Ala Leu Ser Leu Trp Ser Glu Ser Leu Ile Gln Val
    450                 455                 460 ctc tag                                                                  1398
Leu
465

<210> SEQ ID NO 3
<211> LENGTH: 1398
<212> TYPE: DNA
<213> ORGANISM: Rattus norvegicus

<400> SEQUENCE: 3 atg cca aag aaa gtg aag ccc aca ggg gat gag aat gaa gaa gag tct           48
Met Pro Lys Lys Val Lys Pro Thr Gly Asp Glu Asn Glu Glu Glu Ser
                5                   10                  15 gtt cct tgc aag cag gtg aaa gag gag cta cct aat acg ctt tct gta           96
Val Pro Cys Lys Gln Val Lys Glu Glu Leu Pro Asn Thr Leu Ser Val
            20                  25                  30 tta aac ttt gac agc ccc agt agt ttc ttt gaa agt tta ata tca ccc          144
Leu Asn Phe Asp Ser Pro Ser Ser Phe Phe Glu Ser Leu Ile Ser Pro
        35                  40                  45 atc aaa gta gag aca ttt ttc aag gaa ttc tgg gaa cag aag ccc ctt          192
Ile Lys Val Glu Thr Phe Phe Lys Glu Phe Trp Glu Gln Lys Pro Leu
    50                  55                  60 ctc att cag aga gat gac cct tcg ctg gcc gca tat tac cag tct ctg          240
Leu Ile Gln Arg Asp Asp Pro Ser Leu Ala Ala Tyr Tyr Gln Ser Leu
65                  70                  75                  80 ttc agc ctc tca gat ctg agg agt ctc tgc agc caa ggg ctg tac tat          288
Phe Ser Leu Ser Asp Leu Arg Ser Leu Cys Ser Gln Gly Leu Tyr Tyr
                85                  90                  95 gga aga gat gtc aat gtc tgc cgg tgc atc ggt ggg aag aag aag gtt          336
Gly Arg Asp Val Asn Val Cys Arg Cys Ile Gly Gly Lys Lys Lys Val
            100                 105                 110 tta aat aag gat ggc aaa gca cag ttt ctt cag ctg aga aaa gat ttt          384
Leu Asn Lys Asp Gly Lys Ala Gln Phe Leu Gln Leu Arg Lys Asp Phe
        115                 120                 125 gat cag aag agg gca aca att cag ttt cat cag cca cag aga ttt aag          432
Asp Gln Lys Arg Ala Thr Ile Gln Phe His Gln Pro Gln Arg Phe Lys
```

|   |   |   |   |   |   |   |   |   |   |   |   |   |   |   |   |     |
|---|---|---|---|---|---|---|---|---|---|---|---|---|---|---|---|-----|
| Asp | Gln | Lys | Arg | Ala | Thr | Ile | Gln | Phe | His | Gln | Pro | Gln | Arg | Phe | Lys |   |
|   | 130 |   |   |   | 135 |   |   |   | 140 |   |   |   |   |   |   |   |

```
gat gag ctc tgg agg atc cag gaa aag ctg gaa tgt tac ttt ggc tcc      480
Asp Glu Leu Trp Arg Ile Gln Glu Lys Leu Glu Cys Tyr Phe Gly Ser
145             150                 155                 160 tta gta ggc tca aat gtg tac atg act ccc gca gga tct cag ggc ctt      528
Leu Val Gly Ser Asn Val Tyr Met Thr Pro Ala Gly Ser Gln Gly Leu
                165                 170                 175 cct cca cat tac gac gat gtt gag gtt ttt atc ctg cag ctg gag gga      576
Pro Pro His Tyr Asp Asp Val Glu Val Phe Ile Leu Gln Leu Glu Gly
            180                 185                 190 agg aaa cgt tgg cgc ctg tac tcc cca act gtg ccc ctg gcg cgt gag      624
Arg Lys Arg Trp Arg Leu Tyr Ser Pro Thr Val Pro Leu Ala Arg Glu
        195                 200                 205 tac agt gtg gag cct gag gac cgg att ggc aca cca aca cat gac ttc      672
Tyr Ser Val Glu Pro Glu Asp Arg Ile Gly Thr Pro Thr His Asp Phe
    210                 215                 220 ctg ctg aag cct ggc gat ttg ttg tac ttc ccc aga ggg acc att cac      720
Leu Leu Lys Pro Gly Asp Leu Leu Tyr Phe Pro Arg Gly Thr Ile His
225                 230                 235                 240 cag gca gaa act cct tca ggc ctg gcc cac tct att cac ctg act att      768
Gln Ala Glu Thr Pro Ser Gly Leu Ala His Ser Ile His Leu Thr Ile
                245                 250                 255 agc acc tac cag aac aat tca tgg gga gat tac ctt ttg gac tcc att      816
Ser Thr Tyr Gln Asn Asn Ser Trp Gly Asp Tyr Leu Leu Asp Ser Ile
            260                 265                 270 tcg ggg ctt gta ttt gac att gca aag gaa gat gtg gca tta agg act      864
Ser Gly Leu Val Phe Asp Ile Ala Lys Glu Asp Val Ala Leu Arg Thr
        275                 280                 285 gga atg ccc agg cgg atg ctc atg aat gtg gaa acc cca gct gac gta      912
Gly Met Pro Arg Arg Met Leu Met Asn Val Glu Thr Pro Ala Asp Val
    290                 295                 300 aca agg aag ttg agt ggc ttt ctg agg act ctg gca gac cag ctc gag      960
Thr Arg Lys Leu Ser Gly Phe Leu Arg Thr Leu Ala Asp Gln Leu Glu
305                 310                 315                 320 ggc aga aaa gaa ctg ctc tca tca gat atg aag aag gac ttc gtc atg     1008
Gly Arg Lys Glu Leu Leu Ser Ser Asp Met Lys Lys Asp Phe Val Met
                325                 330                 335 cac aga ctt ccc cct ttc tgt gtg gga aat gga aca gag tca atg aac     1056
His Arg Leu Pro Pro Phe Cys Val Gly Asn Gly Thr Glu Ser Met Asn
            340                 345                 350 cca ggt gga aag ttg cca agg ttg aac agc ata gta aga ctg cag ttt     1104
Pro Gly Gly Lys Leu Pro Arg Leu Asn Ser Ile Val Arg Leu Gln Phe
        355                 360                 365 aaa gac cac att gtc ctc aca gta ggg ccc gat cag aat caa tct gat     1152
Lys Asp His Ile Val Leu Thr Val Gly Pro Asp Gln Asn Gln Ser Asp
    370                 375                 380 gaa gct caa caa aag gtg gtt tac atc tac cat tct cta aag aat gag     1200
Glu Ala Gln Gln Lys Val Val Tyr Ile Tyr His Ser Leu Lys Asn Glu
385                 390                 395                 400 aga cag acg cac atg atg ggg aaa gag gtg gaa aca gag att tat gga     1248
Arg Gln Thr His Met Met Gly Lys Glu Val Glu Thr Glu Ile Tyr Gly
                405                 410                 415 ctt cgc ttt cct tta tcc tat gtg gac gct ctg aag caa atc tgg tgc     1296
Leu Arg Phe Pro Leu Ser Tyr Val Asp Ala Leu Lys Gln Ile Trp Cys
            420                 425                 430 ggg tca cca gtt cgt gtt aag gac ctg aaa ctt ggc aca gat gaa gag     1344
Gly Ser Pro Val Arg Val Lys Asp Leu Lys Leu Gly Thr Asp Glu Glu
        435                 440                 445
```

-continued

| aag | gag | aac | ctg | gca | gtg | tct | ctc | tgg | aca | gag | tgt | cta | gtc | cac | gtg | 1392 |
| Lys | Glu | Asn | Leu | Ala | Val | Ser | Leu | Trp | Thr | Glu | Cys | Leu | Val | His | Val | |
| | 450 | | | | | 455 | | | | | 460 | | | | | |

| ctc | tag | | | | | | | | | | | | | | | 1398 |
| Leu | | | | | | | | | | | | | | | | |
| 465 | | | | | | | | | | | | | | | | |

CANCER ASSOCIATED GENE MINA 53, PROTEIN MINA 53 AND MONOCLONAL ANTIBODY THEREOF

This application is a U.S. national stage of International Application No. PCT/JP03/04699 filed Apr. 14, 2003.

TECHNICAL FIELD OF THE INVENTION

The present invention relates to a cancer-associated gene mina53, a protein Mina53 and a monoclonal antibody thereof.

BACKGROUND OF THE INVENTION

Cancer is a cell tumor which is led to automatically mortal death, and causes a large percentage, that is apt to increase, of human deaths. Cancer cells are originally normal cells, and when the genes of normal cells are damaged by certain causes such as chemical substances, radiation or infection with virus and the like and the damaged DNA is not repaired, the accumulation of such DNA in the normal cell induces the normal cells to become cancerous. Generally, cells possess the functions for restoration of the damaged genes. If such systems are not working normally, irregular genes are accumulated. Various cancer-associated genes have already been found and there include cancer genes which accelerate cancer and cancer-inhibitory genes which suppress cancer.

It is known that the pre-cancer gene myc family is one family of such cancer-associated genes particularly related to cancer. Such family members are cell proliferation-associated genes which play an important role in cancer and ontogeny and the like, and abnormalities of myc gene have been found in human cancer at a very high ratio.

The cancer gene c-myc family consists mainly of three genes, c-myc, N-myc, and L-myc. Although the three genes exhibit distinct patterns of expression and timing, they appear to have basically the same biological activity. The expression of cancer gene c-myc is highly regulated at the level of transcription or after transcription and the like. Generally, the expression of c-myc is associated with cell proliferation and expression is reduced in the cell at interphase or during differentiation. Deregulated expression of myc family genes, through gene amplification, viral promoter insertion, chromosomal translocation, or promoter mutation is associated with neoplastic diseases in a wide range of vertebrates including humans (DePinho, R. A., et al.: (1991) Adv. Cancer Res. 57, 1-46; Marcu, K. B., et al.: (1992) Annu. Rev. Biochem. 61, 809-860; Morgenbesser, S. D., et al.: (1994) Semin. Cancer Biol. 5, 21-36; Henriksson, M., et al. (1996) Adv. Cancer Res. 68, 109-182; Grandori, C., et al.: (2000) Annu. Rev. Cell Dev. Biol. 16, 653-69). Embryonic mice with c-myc or N-myc deleted develop multi-organ hypoplasia and die during mid-embryogenesis (Stanton, B. R., et al.: (1992) Genes Dev. 6, 2235-2247; Sawai, S., et al.: (1993) Development 117, 1445-1455; Davis, A. C., et al.: (1993) Genes Dev. 7, 671-682). These results indicate that myc is the central regulator of cell growth (Henriksson, M., et al. (1996) Adv. Cancer Res. 68, 109-182; Grandori, C., et al.: (2000) Annu. Rev. Cell Dev. Biol. 16, 653-69; Lüscher, B.: (2001) Gene 277, 1-14).

These cancer genes, myc family genes encode the transcription factor (Myc protein) which regulates the expression of various genes (Grandori, C., et al.: (2000) Annu. Rev. Cell Dev. Biol. 16, 653-69; Lüscher, B.: (2001) Gene 277(October 17; (1-2):), 1-14). The protein encoded by myc family genes is a member of the basic helix-loop-helix leucine zipper (bHLHLZ) transcription factors. Dimerization of Myc protein with its obligate partner Max results in the formation of a heterodimer having sequence-specific DNA binding activity. The dimer binds to E-box sites (mainly CACGTG elements) through the basic part. The myc has another domain, the transcriptional activation domain and activates transcription of various genes by activities of these domains. Such Myc target genes (Dang, C. V. (1999) Mol. Cell. Biol. 19, 1-11) as ODC (Bello-Fernandez, C., et al.: (1993) Proc. Natl. Acad. Sci. USA 90, 7804-7808), cdc25A (Galaktionov, K., et al.: (1996) Nature 382, 511-517), RCC1 (Tsuneoka, M., et al.: (1997) Oncogene 14, 2301-2311), cyclin D2 (Bouchard, C., et al.: (2001) Genes & Dev. 15, 2042-2047), and Id2 (Lasorella, A., et al.: (2000) Nature 407, 592-598) have been identified. Attempts to identify genes capable of re-establishing normal proliferation by introducing an expression gene library to cells which the functional c-myc gene are completely lost have resulted in the repeated identification of c-myc and N-myc, other genes could not be identified. These results suggest that myc controls not a gene but genes to regulate cell proliferation. However, enough Myc target genes to elucidate the function of cancer gene myc have not been identified yet and therefore, the mechanism for demonstrating myc functions has not been satisfactorily clarified. Accordingly, the identification of the new genes expressed and regulated by myc can help elucidate the function of cancer gene myc.

Colon cancer is among the most frequent neoplasms in western countries. It is currently thought that most colon cancers develop from preexisting adenomas, although some may emerge de novo (Fearon E R, Vogelstein B: Cell 1990, 61:759-767; Kuramoto S, Oohara T: Cancer 1989, 64:950-955; Bedenne L., et al.: Cancer 1992, 69:883-888; Wada R, et al.: Cancer 1996, 77:44-50). Most colon cancers are known to progress through a gradual series of histological changes from normal state to premalignant (adenoma) and malignant stages (Fearon, E. R., Vogelstein, B.: ibid; Vogelstein, B., Kinzler, K. W.: Trends Genet 1993, 9: 138-141; Kinzler, K. W., Vogelstein, B.: Cell, 1996, 87: 159-170). In the course of cancer progress, it is considered that poorly differentiated (hereinafter referred to as "poor differentiation") tumor generally progress faster than moderately differentiated (hereinafter referred to as "moderate differentiation") tumor or more differentiated, namely well differentiated (hereinafter referred to as "well differentiation") tumor.

Studies for elucidation of colon cancer-associated gene have shown that loss of function of tumor suppressor genes as well as activation and abnormal expression of oncogenes are responsible for carcinogenesis. It is reported that the proto-oncogene myc family, c-myc is overexpressed in most human colon cancers (Stewart, J., et al.: Br. J. Cancer 1986, 53: 1-6; Siroka, K., et al.: Cancer 1987, 59: 1289-1295) and most of which harbor mutations in the tumor suppressor adenomatous polyposis coli (APC) gene (Cottrell, S., et al.: Lancet 1992, 340: 626-630; Miyoshi, Y., et al.: Hum Mol Genet 1992, 1: 229-233; Powell, S. M., et al.: Nature 1992, 359: 235-237).

Recently, c-myc was specified as the target of the APC pathway and provided a molecular framework for understanding the overexpression of c-myc in colon cancers (He, T. C., et al.: Science 1998, 281: 1509-1512). This framework is supported by the observation that the expression of c-myc is either induced by loss of function of the APC gene or suppressed by the functional APC gene product.

In spite of intensive efforts to investigate the role(s) of c-myc in carcinogenesis, the mechanisms by which deregulation of c-myc gene expression contributes to carcinogenesis are still not fully resolved, and many aspects are still enigmatic (Lutz, W., et al.: Biochem Biophys Acta 2002, 1602: 61-71). c-myc gene is a multifunctional gene, and its functions include cell division, cell growth, and apoptosis. c-myc gene appears to control the expression of several genes that mediate each of the above functions, some of which may contribute to carcinogenesis. Functional information and expression patterns of novel genes controlled by c-myc gene may therefore contribute to a better understanding of carcinogenesis induced by c-myc gene.

In addition to colon cancers, esophageal cancer is one of the popular cancers in Japan. The number of patients drastically increases with aging. At present, the number of patients who die as a result of esophageal cancer is almost 3% of the total number of patients who die as a result of cancer. As the society population ages, it is expected that there will be more cases of esophageal cancer. Thus, esophageal cancer is an important disease in view of the health of nations.

The studies for elucidation of esophageal cancer-associated genes show that the loss of function of the tumor suppressor gene, the activation of tumor gene, and abnormality of expression are involved in carcinogenesis and the abnormal expression of c-myc has also been reported (Kennedy A R: Cancer Res. 1994, 54 (7 Suppl): 1999s-2005s).

The present inventors have searched genes which c-myc caused increased expression by a cDNA micro-array method. As a result, the novel cancer-associated gene of the present invention has been identified. c-Myc protein binds with the promoter sites which regulate the expression of the gene and makes the expression of this gene directly increase (Tsuneoka, M., et al.: J Biol Chem 2002, 277: 35450-35459). Leukemia cell line HL60 was treated with TPA (phorbol 2-myristate 13-acetate) to reduce expression of c-myc and prevent cell proliferation. Then, cell extracts of the leukemia cell line HL60 either treated or untreated with TPA were examined by a polyclonal antibody having a specificity to cancer-associated gene-encoding protein to confirm that the expression of the protein is reduced by TPA (Tsuneoka, M., et al: J Biol Chem 2002, 277: 35450-35459).

This protein was visualized by indirect immunofluorescence staining with specific antibody which indicated that it is localized in cellular nucleus. This protein has been named Mina53 and its gene has been named mina53 based on myc-induced nuclear antigen having 53 kDa of molecular weight.

Therefore, based on the knowledge by the above-mentioned arts, the present inventors believe that studies of the functional information and expression pattern of cancer-associated mina53 gene regulated by c-myc gene and its Mina53 protein using anti-Mina53 monoclonal antibody against Mina53 protein are useful for elucidation of carcinogenesis by c-myc gene.

The present inventors have made intensive research efforts to identify a Myc target gene in order to explain the function of c-myc cancer gene. As a result, they succeeded in producing anti-Mina53 monoclonal antibody against Mina53 protein (hereinafter referred to as "anti-Mina53 monoclonal antibody"). The present inventors have found that the expression of Mina53 protein in colon cancer cells is increased as compared to normal colon tissues by using anti-Mina53 monoclonal antibody, and further that the expression of Mina53 protein is an early event in colon cancer and specific character. The inventors have also found that Mina53 suggests the probability that plays a certain role in carcinogenesis of colon cancer. These results demonstrate that Mina53 protein can be used as a marker against, particularly, colon cancer and that there is a possibility to develop it as a target for the treatment of colon cancer diseases. Furthermore, it can also be used as a marker against esophageal cancer, and there is a possibility to develop it as a target for the treatment of esophageal cancer diseases. These have completed the present invention.

DISCLOSURE OF THE INVENTION

The purpose of the present invention is to provide a human, mouse and rat mina53 gene, and a human, mouse and rat Mina53 protein as the Myc target gene which can be used to explain the function of cancer gene myc.

Another purpose of the present invention is to provide a mina 53 gene-encoding plasmid and reporter plasmid.

Further, another purpose of the present invention is to provide a method for inhibiting the proliferation of cancer cells by such novel Myc target gene.

Also, another purpose of the present invention is to provide an antibody obtainable from mina53 gene, or human Mina53 protein or fragment thereof as an antigen.

Furthermore, a purpose of the present invention is to provide a monoclonal antibody (hereinafter referred to as "anti-Mina53 monoclonal antibody") having specificity to Mina53 protein.

Another purpose of the present invention is to provide a method for detecting Mina53 protein that comprises detecting Mina53 protein in cancer cells or cancer tissues using anti-Mina53 monoclonal antibody.

Further, another purpose of the present invention is to provide a method for staining Mina53 protein that comprises staining Mina53 protein expressed in cancer cells or cancer tissues using anti-Mina53 monoclonal antibody.

In addition thereto, another purpose of the present invention is to provide a method for diagnosis of cancer by staining Mina53 protein expressed in cancer cells or cancer tissues using anti-Mina53 monoclonal antibody.

In order to achieve the above-mentioned purposes, the present invention provides novel cancer-associated gene as Myc target gene.

As one embodiment of the present invention, the present invention provides cancer-associated mina53 gene whose expression is directly regulated by cancer myc gene and which encodes nuclear protein having nucleotide sequence and amino acid sequence shown by the SEQ ID NO: 1 of the Sequence Listing and having a 53 kDa molecular weight. Also, the present invention provides cancer-associated mina53 gene that is associated with the proliferation of cancer cells and of which expression specifically increases in cancer tissues as the preferable embodiment of the present invention. Further, the present invention provides the cancer-associated mina53 gene which is located in nucleus and nucleoli, and of which expression is induced by c-myc gene as another preferable embodiment.

Further, the present invention provides a human Mina53 protein having an amino acid sequence shown in SEQ ID NO: 1 and exhibiting cell proliferation activity.

Accordingly, mina53 gene and Mina53 protein of the present invention can be used in various fields by employing these functions.

The present invention also provides mouse cancer-associated mina53 gene having a nucleotide sequence shown by SEQ ID NO: 2 or rat cancer-associated mina53 gene having a nucleotide sequence shown by SEQ ID NO: 3. Mouse cancer-associated mina53 gene having a nucleotide sequence shown by SEQ ID NO: 2 and rat cancer-associated mina53 gene having a nucleotide sequence shown by SEQ ID NO: 3 are useful to investigate their cell proliferating activity.

As another embodiment of the present invention, a plasmid encoding the cancer-associated gene mina53 of the present invention is provided. The present invention also provides a reporter plasmid having a mina53 genomic DNA fragment as another embodiment.

Further, the present invention provides a method for regulating the expression of cancer-associated mina53 gene.

Furthermore, an antibody against Mina53 protein is provided as another embodiment of the present invention. The antibody of the present invention can be, for example, used for the diagnosis of cancer and the treatment of cancer, and for the diagnosis of abnormal cells such as cancer cells and the diagnosis of the condition of cells.

Namely, the present invention provides an anti-Mina53 monoclonal antibody which is specific to Mina53 protein, particularly human Mina53 protein.

The present invention provides a method for detecting Mina53 protein which comprises detecting Mina53 protein in cancer cells or cancer tissues by using anti-Mina53 monoclonal antibody as the other embodiment.

As the preferable embodiment of the present invention, a method for detecting Mina53 protein that comprises detecting Mina53 protein in colon cancer cells or colon cancer tissues is provided.

Further, the present invention provides a method for staining Mina53 protein which comprises staining Mina53 protein expressed in cancer cells or cancer tissues by using anti-Mina53 monoclonal antibody as another embodiment. Further, the present invention provides a method for staining Mina53 protein which comprises staining Mina53 protein expressed in colon cancer cells or colon cancer tissues, or esophageal cancer cells or esophageal cancer tissues with anti-Mina53 monoclonal antibody as the more preferable embodiment.

Another embodiment of the present invention provides a diagnostic method for cancer that comprises diagnosing cancer by staining Mina53 protein expressed in cancer cells or cancer tissues with anti-Mina53 monoclonal antibody. The preferable embodiment of the present invention provides a method for diagnosing colon cancer or esophageal cancer by staining Mina53 protein with anti-Mina53 monoclonal antibody.

Other purposes, characteristics and advantages of the present invention can be obviously understood based on the following descriptions of the present specification.

BRIEF DESCRIPTION OF DRAWINGS

FIG. 1A shows the genomic organization of human mina53, FIG. 1B shows the reporter plasmids, and FIG. 1C shows the result of the transient expression assay using T98Gmycer-2 cells.

FIG. 2A shows the correlation of mina53 mRNA levels with c-myc expression levels in T98G cells, FIG. 2B shows the correlation between the decrease in mina53 mRNA levels and c-myc mRNA disappearance in human promyelocytic leukemia HL60 cells, and FIG. 2C shows the inducement of mina53 mRNA expression in the MycER protein-expressed T98G cells (T98Gmycer-2 cells).

FIG. 3B shows the change of the expression of Mina53 protein by expressing human c-Myc or mutant c-Myc deleted the increasing ability of the expression of genes in rat cells.

FIG. 5A shows the reduction of Mina53 protein expression by RNA interference, and FIG. 5B shows the cell proliferation of cells with decreased Mina53 protein expression by RNA interference. In the Figures, the symbol ● shows the state that the cells were transfected with siRNA duplexes specific for human mina53, the symbol ▲ shows the state that the cells were transfected with siRNA duplexes specific for rat mina53, and the symbol ○ shows the state that the cell were transfected with control siRNA.

FIG. 7A shows HE staining of a section that contained a moderately differentiated tumor. FIG. 7B shows the serial section of FIG. 7A stained by anti-Mina53 monoclonal antibody showing elevated expression of Mina53 in the cancer area but little staining in the adjacent non-neoplastic tissues. FIG. 7C shows the serial section of FIG. 7A stained by anti-Ki-67 antibody. FIG. 7D shows the control section of FIG. 7A in which the primary antibody was omitted. FIG. 7E shows enlargement of the section shown in FIG. 7B exhibited the characteristic nuclear localization of Mina53. FIG. 7F shows staining of a poorly differentiated tumor by anti-Mina53 monoclonal antibody. In the Figures, scale bars are 300 μm (FIGS. 7A to D), 50 μm (FIG. 7E) and 75 μm (FIG. 7F).

FIG. 8A shows cancer cells that have penetrated into lymphatic vessels beneath the epithelium stained by anti-Mina53 monoclonal antibody. FIG. 8B shows cancer cells in lymphatic vessels in deeper layers of the colon stained by anti-Mina53 monoclonal antibody. FIG. 8C shows staining of a deeply invading tumor cells. FIG. 8D shows tumor cells in fibrous substrates stained by anti-Mina53 monoclonal antibody. Scale bars are 75 μm (FIGS. 8A and 8D), 150 μm (FIG. 8B) and 300 μm (FIG. 8C).

FIG. 9A shows the comparison of staining of Mina53 with that of Ki-67 (FIG. 9B) in well-differentiated tumor. FIG. 9C shows the comparison of staining of Mina53 with that of Ki-67 (FIG. 9D) in adenocarcinoma. FIG. 9E shows the comparison of staining of Mina53 with that of Ki-67 (FIG. 9F) for the epithelial cells in normal crypts. FIG. 9G shows the comparison of staining of Mina53 with that of Ki-67 (FIG. 9H) in the germinal center of lymphatic follicle. Scale bars are 75 μm (Figures A to F) and 150 μm (FIGS. 9G and 9H).

BEST MODE FOR CARRYING OUT THE INVENTION

The human genomic DNA sequence containing cDNA sequence of cancer-associated mina53 gene can be retrieved by HTGS (GenBankAcc: AC026100, AC073245, AC024892). Since the length of intron 2 (between exon 2 and exon 3) was controversial between the GenBank data, the genomic DNA fragment was amplified by PCR using oligonucleotides corresponding to the sequences in exon 2 and exon 3 as primers, and the length of intron 2 was determined to be 5.2 kb.

Figure 1:
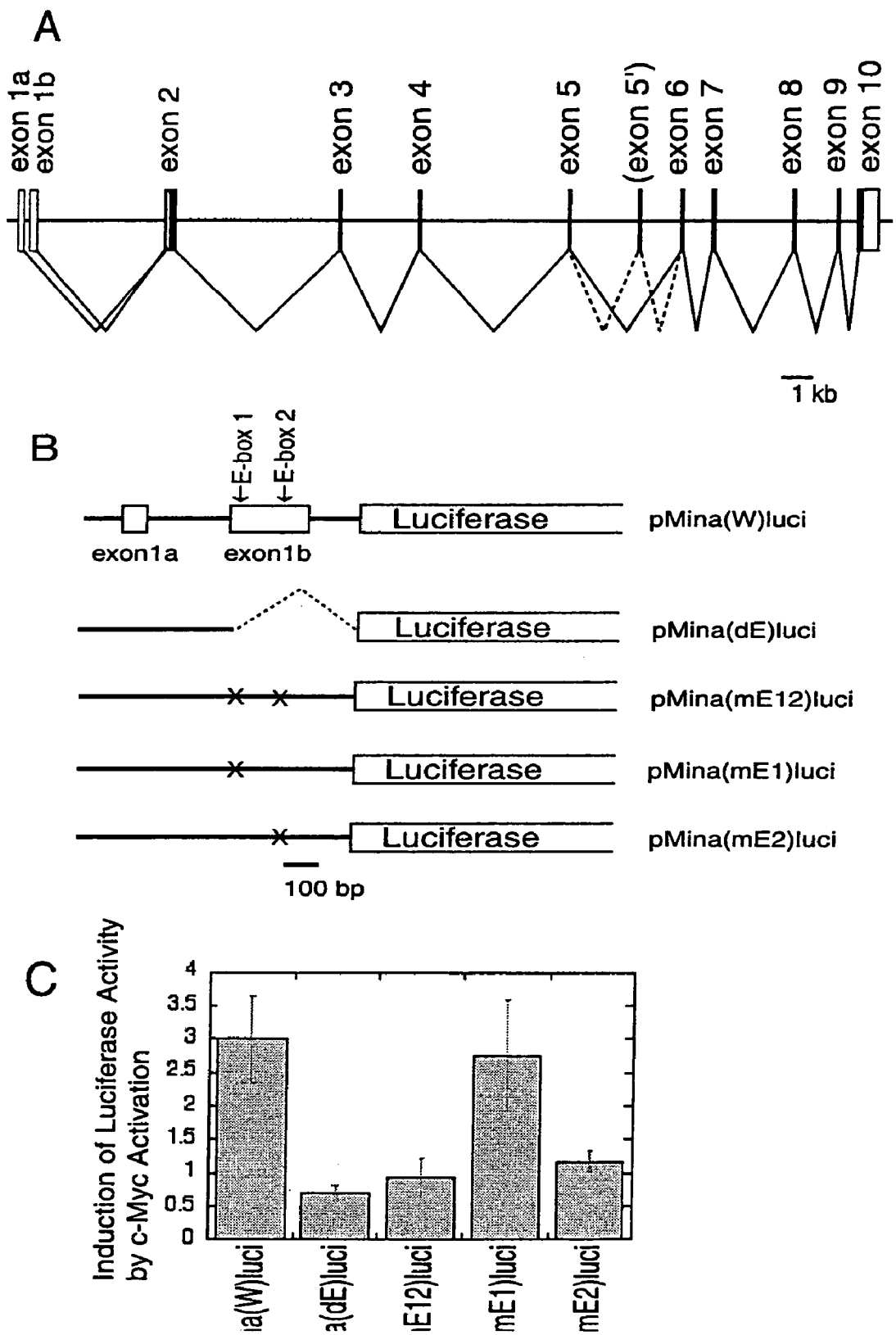
FIG. 1 shows the gene structure of human mina53 of the present invention.

Cancer-associated mina53 gene of the present invention possesses the nucleotide sequence and amino acid sequence shown by SEQ ID NO: 1 of the Sequence Listing. In more detail, as shown in FIG. 1, human mina53 gene among the cancer-associated mina53 gene consists of twelve exons, exon 1a and exon 1b is present in the upstream region as two transcription initiation sites, the translation initiation site is located in exon 2, and the stop codon (TAG) exists in the last exon 10. Exon 1b exists 0.25 kb downstream of the exon 1a. Further, 101 bp cDNA sequence inserted in the center of main cDNA, namely between exon 5 and exon 6 exists as exon 5'. cDNA encoding 464 amino acids lacking 297Q lacks the first 3 bp of exon 7. The mapping data of UCSC-GenomeBrowser showed that mina53 gene mapped to the third chromosome (3q12.1).

Furthermore, the expression of the cancer-associated mina53 gene of the present invention is directly induced by cancer gene c-myc, and the cancer-associated mina53 gene encodes a protein having the molecular weight of 53 kDa and such protein is present in nucleoplasma and nucleoli. The specific inhibition of the expression induces the significant suppression of cell proliferation.

Using cDNA micro array method can identify the novel mina53 gene of the present invention. The micro array method employed includes various procedures widely used in the art such as DNA chip (cDNA micro array). For example, total RNA can be isolated from untreated T98Gmycer-2 cell (mentioned hereinafter) and the same cell which was treated with 4-hydroxytamoxifen(OHT) as an estrogen derivative for 20 hours. Poly(A+) RNA was recovered and subjected to differential display using a commercially available DNA chip. 9000 or more kinds of cDNAs including EST (Expression Sequence Tagged) clones can be plated. Naturally, the present invention should be construed to not be limited by such art and any arts which can be used in such arts can be adopted.

The plasmid for encoding c-myc that is used in the present invention can be prepared by the conventional manner in said arts. The plasmids used are commercially available, and can be appropriately selected according to the purposes. The plasmid encoding c-myc used in the present invention includes, for example, Pc-myc/CDM8 (Tsuneoka, M. et al. (1997) Oncogene 14, 2301-2311) obtained by expressing and inducing human c-myc with CMV promoter or pc-mycer/CAGGS in which c-mycer is driven by a chimeric promoter consisting of chicken actin and CMV promoters prepared by digesting the same and self-ligating to produce pc-myc (d41-178)/CDM8, which encodes a mutant c-Myc protein lacking the activated domain. The BstXI-KpnI fragment of pc-myc (d41–178)/CDM8 and pTc-mycer/BS as inserted into EcoRI fragment of pCAGGS mammalian expression vector.

The plasmids encoding mina53 of the present invention can be also prepared by a conventional manner widely used in the arts. The plasmids used are commercially available and can be selected appropriately.

For example, cDNA for human mina53 was amplified by PCR with 5'-GAAGCTTATGCCAAAGAAAGCAAAGC-CTACAGG-3' (SEQ ID NO: 4), adding a HindIII site just before the initiation methionine, and 5'-TGAATTCATC-CTCTCCTCGGCTCAGGTCTT-3' (SEQ ID NO: 5) as primers from a library of human erythroid leukemia cells (HEL), and the amplified fragment was cloned into a specific vector to produce pT/hmina53 (465) and pT/hmina53 (464), encoding 465- and 464-amino acid proteins, respectively. The pEGGFP/hmina53 (465), which is prepared GFP-Mina53 fusion protein, was obtained from the HindIII-SalI fragment of pT/hmina53 (465). The phmina53/Rc/CMV can be produced from the HindIII-NotI fragment of pT/hmina53 (465), which was digested with HindIII and NotI. The DNA fragment encoding human mina53 was amplified by PCR with 5'-GCCATGCCATGGCAAAGAAAGCAAAGC-CTAC-3' (SEQ ID NO: 6), designed to have an artificial NcoI site, and 5'-GGCATGCCATGGCTAGACTACT-TGAATTAAAC-3' (SEQ ID NO: 7), adding an NcoI site, as primers from pEGFP/hmina53 (465). The amplified fragment was cleaved with NcoI and ligated with an *E. coli* expression vector pET to produce pET/hmina53. The XhoI-SalI fragment of pEGFP/hmina53 (465) was inserted into a vector to produce pGEX-hmina53 (GST-Mina53 fusion protein).

To investigate promoter activity of the mina53 gene, a human mina53 genomic DNA fragment including a specific part was joined to luciferase cDNA to construct a reporter plasmid by a conventional manner. Transient expression assays in T98G cells indicate that the DNA fragment has promoter activity.

The present invention indicates that c-Myc directly regulates the expression of mina53 gene. T98G cells under serum-starvation condition were activated by serum to increase the level of c-mycmRNA and consequently increase mina53. The expression of c-myc was reduced by TPA in HL60 cells to induce the reduction of the expression of mina53 mRNA and protein. The wild type c-Myc, not mutant c-Myc lacking transcriptional activation domain in the rat fibroblast 3Y1 cell lines, was highly expressed to increase the expression of mina53. c-Myc protein was activated in c-MycER chimeric protein to activate the expression of mina53 mRNA and protein. The induction of mina53 mRNA by the activation of c-MycER maintained in the presence of cycloheximide as the protein synthesis inhibitor. In the transient expression assays, the expression from reporter plasmids constructed based on the fragment of human mina53 genomic DNA increased by the activation of c-MycER. When the putative Myc binding sites (E-box 1: CACGTG element) in the reporter plasmid were destroyed, the stimulation of the reporter plasmid gene expression by c-myc was abolished. Although a mutation of one of the CACGTG elements (E-box 1) had little effect, the mutation of the other CACGTG element (E-box 2) severely decreased the elevation of promoter activity by c-Myc, suggesting that c-Myc activates the mina53 expression through a specific CACGTG element. c-Myc protein binds to the mina53 genomic DNA that contains the E-box 2 in vivo in proliferating HL60 cells but not HL60 cells treated with TPA. These results demonstrate that c-Myc directly induces the expression of mina53.

The novel mina53 gene of the present invention possesses the function for regulating the cell proliferation. The high conservation of amino acid sequences of Mina53 protein between human and rodents suggest that the protein plays an important role in mammals. The expression of mina53 correlated well with cell proliferation, suggesting a role of mina53 in cell proliferation. To investigate the biological function of Mina53, a new technique, small interference RNA (siRNA) technique, was applied to inhibit specifically the expression of mina53. Specific inhibition of Mina53 expression by siRNA duplex was clearly shown here because the expression of Mina53 protein in human and rat cells was specifically reduced by each cognate siRNA duplex for human and rat mina53, respectively, but not by a control siRNA (inverted sequence for human mina53) or a duplex directed against mina53 of different species. When the expression of Mina53 protein was reduced, severe inhibition of cell proliferation was observed in both human and rat cells. These results indicate the importance of mina53 in proliferation of mammalian cells.

In vivo studies in mice in which c-myc expression is incrementally reduced to zero shows that c-myc gene possesses the action to result in reduced body mass owing to multi-organ hypoplasia (reducing cell numbers) by the reduction of c-Myc levels. c-Myc activity determines the ratio of activated T cells that re-enter the cell cycle and the rate of cell division of fibroblasts. A recent in vitro study using time-lapse microscopy also suggested that c-myc gene regulates the decision of cells to enter or exit the cell cycle in rat cell culture systems. Some genes directly involved in the cell cycle machinery including cyclin D1, cyclin D2 and Id2 and the like were identified as Myc target genes and the results consistent with these were shown. Mice with one of these genes deleted showed more gentle result than that of mice with c-myc deleted. On the other hand, when the expression gene library was introduced into cells lacking their functional c-myc thoroughly, genes, which re-establish normal proliferation, could not be identified, only c-myc and N-myc identified repeatedly. These results indicate that myc gene regulates cell cycle through controlling several genes, not a single gene. Moreover, the present invention shows that mina53 is one of the target genes of c-Myc, and regulates cell proliferation. Therefore, it is possible that Mina53 protein may function by interacting directly on cell cycle machinery factors such as cyclin D1, cyclin D2 and Id2. Recent studies suggest that the nucleolus might function as a prison for certain proteins involved in eukaryotic cell cycle regulation. Sequestration of proteins into nucleoli prevents them from reaching their targets in other regions of the cell.

Mina53 protein exists in nucleus, in particular concentrate in nucleoli. The location of Mina53 in nucleoli may suggest one form of the regulation of the activity of Mina53 protein.

It was shown that loss of *Drosophila* Myc (dMyc) retards cellular growth (accumulation of cell mass) and reduces cell size, whereas dMyc overproduction increases growth rate and cell size, suggesting that dMyc regulates a gene involved in cellular growth. Increase of the expression of Myc and cell size was observed in mammals. For example, transgenic mouse which expressed c-myc under control of the immunoglobulin heavy-chain enhancer resulted in an increase in cell size of pretransformed B-lymphocytes at all stages of B cell development. This increase correlated with an increase in protein synthesis. The ribosome biogenesis is essential for cell proliferation and nucleolus has been considered to be a "ribosome factory" since the 1960s. Recent reports also suggest that myc enhances the expression of a large set of genes functioning in ribosome biogenesis. Thus, the location of Mina53 in nucleoli suggests that mina53 may play a necessary role in ribosome biogenesis.

It is suggested that the nucleolus is involved in many other aspects, including the processing or nuclear export of certain mRNAs, biogenesis of signal recognition particle RNA and telomerase RNA, and processing one of the spliceosomal small nuclear RNAs. These functions also appear to be essential for cell proliferation. Thus, Mina53 may play a role in one of these functions.

Although no domains whose functions have been experimentally demonstrated are found in Mina53, the amino acid sequence 128-271 of Mina53 represents a JmjC domain, a domain that was recently identified on the basis of significant sequence similarity among many genes. JmjC domains are present in some metalloenzymes that adopt the cupin fold. This domain has been often found together with DNA or chromatin binding domains. This suggests that proteins containing JmjC domain may be enzymes regulating the modeling of chromatin. Also, human, rat and mouse Mina53 in this domain are 87% identical and 72% to 75% of the total sequence is identical. This suggests the functional importance of this domain. Therefore, Mina53 may regulate chromatin remodeling, which appears to largely affect patterns of gene expression.

As stated above, mina53 appears to be an important target of c-myc because of the clear relationship of mina53 with cell proliferation.

The followings are a detailed explanation of anti-Mina53 monoclonal antibody against Mina53 protein of the other embodiment of the present invention (anti-Mina53 monoclonal antibody).

Anti-Mina53 monoclonal antibody of the present invention stains with high sensitivity and can detect Mina53 protein in cancer cells such as colon cancer, sarcoma, tongue cancer, cerebral tumor and the like. Therefore, specific antibody such as anti-Mina53 monoclonal antibody of the present invention, and RNA and DNA possessing the sequence containing mina53 gene can be used to detect Mina53 protein and mRNA encoding Mina53 in the tissues and to detect the abnormal cells such as cancer cells. The amount of the expression of Mina53 protein can be measured, for example, according to the methods such as ELISA method, Western blotting method and the like by using an Mina53 protein binding substance such as polyclonal antibody and monoclonal antibody. The state of cells can, for example, be measured by various measurement methods such as Northern blotting method, RNase protection method, RT-PCR method, cDNA micro array method and the like using RNA or DNA possessing the sequence containing mina53 gene. Further, the presence of abnormal cells such as cancer cells in body or its amount can be estimated or measured to diagnose according to conventional methods in the art such as ELISA method using a polyclonal antibody or a monoclonal antibody against Mina53 protein.

Then, anti-Mina53 monoclonal antibody of the present invention can be prepared according to the conventional methods in the art. Namely, Anti-Mina53 monoclonal antibody of the present invention can be prepared by the fusion method such as a cell fusion method using polyethylene glycol or an electric fusion method, the method using Sendai virus or Epstein-Barr virus and the like or the transformation method with a transformant prepared by a genetic engineering method or with a tumor promoter and the like (Koehler, G., Milstein, C.: Nature 256, 495 (1975)). Particularly, the establishment of a hybridoma by the cell fusion method with polyethylene glycol is preferable.

Then, the establishment of hybridoma by the cell fusion method will be explained in more detail with polyethylene glycol which is preferably used in the present invention.

In the present invention, antigen can be prepared by known methods, for example, by preparing recombinant human Mina53 protein as an immunogen using *E. coli* and the like, and, if necessary, mixing the purified protein obtained with an adjuvant.

Then, the antigen prepared is immunized against an immunized animal. For preparing anti-Mina53 monoclonal antibody, the immunized animal preferably includes mouse and rat which the inbred strains were established in view of the compatibility with myeloma cell line for fusion, and, for example, cattle, horses, goats, sheep, chickens and the like too. The immunization method to the immunized animals can generally be performed by the injection such as subcutaneous, intramuscular or intraperitoneal injections. The amount of administration of the antigen can be determined by appropriately selecting the amount which the desired value of antibody can be obtained and which is not affected inversely against the immunized animals. For accelerating the immune response in immunization, for example, the immunogen can be used with an adjuvant such as Freund's complete adjuvant, Freund's incomplete adjuvant and aluminum hydroxide, if necessary. Particularly, in using a synthesized protein as an immunogen, the substance prepared by binding a carrier protein such as BSA (Bovine Serum Albumin) and KLH (Keyhole Limpet Hemocyanine) and the like with a cross linker.

A hybridoma for producing anti-Mina53 monoclonal antibody of the present invention can be obtained by a conventional manner. Namely, increase of the antibody value was confirmed after final immunization against the immunized animals, and the spleen cells were obtained by taking out the spleen. Hybridomas were prepared by fusing the spleen cells with myeloma cells subcultured alloanimals used for the immunization in the presence of a fusion accelerator. The myeloma cells used include mouse-derived SP2/0-Ag14, P3-NS1-1-Ag4-1, MPC11-45 and 6.TG1.7 and the like, rat-derived 210.RCY.Ag1.2.3 and the like, and human-derived SKO-007 and GM15006TG-A12 and the like and can appropriately be selected. The ratio of the number of the cells of the spleen cells and myeloma cells ranges generally from about 10:1 to about 1:1, preferably from about 4:1 to about 1.5:1.

The fusion accelerator used includes polyethylene glycol and Sendai virus (HVJ), and polyethylene glycol can preferably used in view of the handling and the fusion efficiency, and the polyethylene glycol having about 1,000 to 5,000 average molecular weight is preferable. The concentration of polyethylene glycol in the buffer solution preferably ranges from about 40% to 60% by weight. Further, a supplementary agent such as dimethylsulfoxide and the like can be, if necessary, added to the medium for improving the fusion efficacy.

Cell fusion of the above-mentioned spleen cells with the myeloma cells according to the present invention can be conducted by a conventional manner such as a method for the electric fusion and the like. Generally, both cells were cultivated in the medium for animal cells or in an balanced salt solution, to which the cell fusion agent was added, for example under stirring at a temperature of 37° C. for about 2 minutes. The medium for animal cells used includes, for example, RPMI-1640 medium, Hank's MEM medium (Hank's Minimum Essential Medium), Eagle's MEM medium (Eagle's Minimum Essential Medium) and the like and the balanced salt solution, for example, includes Hank's solution (Hank's balance salt solution) and Earle's solution (Earle's balanced salt solution) and the like.

Hybridomas having a capability for producing anti-Mina53 monoclonal antibody having a specificity against Mina53 protein can be selected from the cell mixture thus obtained in a conventional method as follows: The selection of said hybridoma can be performed by at first separating the hybridoma cell fused by the spleen cells and myeloma cells from cell mixture obtained after operation of cell fusion, and then selecting the hybridoma having an ability for producing antibody specific to Mina53 protein from the separated hybridomas.

More concretely, the separation of the hybridoma from the cell mixture obtained by the above-mentioned operation of cell fusion can be conducted by selectively proliferating the desired hybridoma by cultivating under conditions which only the fused cell can be proliferated among such cell mixture. Generally, the objective hybridoma can selectively be proliferated, for example, by cultivating in the medium for selection such as HAT medium (hypoxanthine/aminopterin/thymidine) and the like. The preferable concentration of the cell mixture in the HAT medium can generally be adjusted in the range of from about $1 \times 10^6$ to $1 \times 10^7$ cells/ml. The cultivation in HAT medium are preferably carried out in air containing about 5 to 8% carbon dioxide at a temperature about 37° C. for about 1 to 4 weeks without stirring.

Then, Hybridoma having a capacity for producing antibody specific to human Mina53 protein was identified from the hybridoma separated as above to select the hybridoma having the capacity for producing the antibody specific to human Mina53 protein. Such method for identification, for example, includes RIA technique, ELIZA technique, plaque technique, spot technique, agglutination reaction method, Ouchterlony technique and the like. Hybridoma thus selected was cloned by, for example, limiting dilution technique to produce hybridoma strain which can be proliferated and possessed the capability for producing anti-Mina53 monoclonal antibody having specificity to Mina53.

The anti-Mina53 monoclonal antibody-producing hybridoma thus produced can recognize human Mina53 protein, can be subcultivated in a conventional medium and can be kept for a long period of time in liquid nitrogen.

The anti-Mina53 monoclonal antibody of the present invention can be recovered from such hybridoma by cultivating the hybridoma according to a conventional manner and obtaining the supernatant or by administrating the hybridoma to the animal which is compatible with the hybridoma, for example the myeloma-providing animal to proliferate and obtaining the ascites.

The anti-Mina53 monoclonal antibody of the present invention can be purified by subjecting the known purification method in the art such as method for ammonium sulfate salting-out method, gel filtration, ion exchange chromatography, affinity chromatography and the like to the antiserum of the immunized animal, the supernatant of hybridoma and the antibody from ascites obtained as above.

The anti-Mina53 monoclonal antibody can be obtained by cultivation of immunized cells in vitro in the presence of human Mina53 protein or its part, producing hybridoma of the immunized cells with myeloma cells using the above mentioned cell fusion technique after fixed intervals and then screening the antibody-producing hybridoma (Reading, C. L.: J. Immunol. Meth., 53, 261 (1982); Pardue, R. L., et al.: J. Cell Biol., 96, 1149 (1983)).

The anti-Mina53 monoclonal antibody of the present invention can express human Mina53 protein in cancer cells and cancer tissues.

The anti-Mina53 monoclonal antibody of the present invention can recognize a single band with a molecular weight of 53 kDa by Western blotting in leukemia cell line HL60. Immunoblotting analysis using the anti-Mina53 monoclonal antibody of the present invention showed that treatment of cells with TPA reduced the signal 53 kDa band. The specificity of the reduction was confirmed because TPA treatment did not significantly reduce β-actin expression.

The present inventors reported previously that the expression of Mina53 is reduced following treatment of HL60 cells with TPA using anti-Mina53 polyclonal antibody (Tsuneoka, M., et al.: J. Biol. Chem. 2002, 277: 35450-35459). It was reported that HL60 cells were terminally differentiated by treatment with TPA in which the c-myc expression level is reduced (Hozumi, M.: Adv. Cancer Res., 1983, 38: 121-169; Hickstein, D. D., et al.: J. Biol. Chem. 1989, 264: 21812-21817)).

Further, it was confirmed that the anti-Mina53 monoclonal antibody yielded a novel single band in addition to the endogenous Mina53 protein in other experiment in which protein fused green fluorescent protein (GFP) expressed in HeLa cells was used.

These results indicate that the anti-Mina53 monoclonal antibody of the present invention recognizes specifically Mina53 protein.

The anti-Mina53 monoclonal antibody of the present invention can detect human Mina53 protein in colon cancer cell lines. For example, as a result of immunoblotting assay by anti-Mina53 monoclonal antibody using 3 kinds of colon cancer cell lines, HT-29, WiDr and SW-620 in the proliferating phase, the anti-Mina53 monoclonal antibody can recognize the single band with a molecular weight of 53 kDa in all of three kinds of cell lines. This shows that these cell lines express Mina53 proteins and that anti-Mina53 monoclonal antibody recognize specifically Mina53 protein in colon cancer cells with no cross-reactivity with other proteins.

The expression level of Mina53 protein in these cell lines is much higher than that of Mina53 protein in HL60 cells experimentally reduced by TPA. The levels of actin in the above three colon cancer cell lines were not higher than that of HL60 cells treated with TPA. These results suggest that the above three colon cancer cell lines contain a higher level of Mina53 protein than terminally differentiated HL60 cells.

According to double immunofluorescence staining of cells using anti-Mina53 monoclonal antibody and anti-nucleolin rabbit antibody, it is confirmed that Mina53 protein is located in colon cancer cells. The anti-Mina53 monoclonal antibody stained specifically nuclei in SW620 cells with strong dotted staining in nucleoli that overlapped with the signals for nucleolin. The other two cell lines also showed a similar pattern of immunofluorescence staining. These results indicate that Mina53 protein locates in the nucleus with concentrated amounts in nucleolus, as the present inventors previously demonstrated in HeLa cells (Tsuneoka, M., et al., ibid).

Furthermore, the anti-Mina53 monoclonal antibody can not only detect Mina53 protein in colon cancer tissues in addition to colon cancer cells, but also Mina53 protein in all pathological grades of colon cancer, namely well, moderately, and poorly differentiated tumors.

EXAMPLES

The present invention will be explained by the following examples, but these examples are described only for the purpose of the explanation of the present invention. Then, these examples are construed not to limit the present invention.

Example 1

Plasmids Encoding c-Myc

Pc-myc/CDM8 (Tsuneoka, M. et al. (1997) Oncogene 14, 2301-2311), in which human c-myc is driven by a CMV promoter, was used. This plasmid was digested with PstI and self-ligated to produce pc-myc (d41-178)/CDM8, which encodes a mutant c-Myc protein lacking the transcriptional activation domain. The 2-kb BstXI-KpnI fragment, blunted with Klenow enzyme, of pTc-mycer/BS was inserted into a 5-kb EcoRI fragment, blunted with Klenow enzyme, and de-phosphorylated with E. coli alkaline phosphatase of a pCAGGS mammalian expression vector to produce pc-mycer/CAGGS in which c-mycer is driven by a chimeric promoter consisting of chicken actin and CMV promoters.

Example 2

Plasmids Encoding Mina53 cDNA for human mina53 was amplified by PCR with 5'-GAAGCTTATGCCAAAGAAAGCAAAGC-CTACAGG-3' (SEQ ID NO: 4), adding a HindIII site just before the initiation codon methionine, and 5'-TGAAT-TCATCCTCTCCTCGGCTCAGGTCTT-3' (SEQ ID NO: 5), as primers from a library of human erythroid leukemia (HEL) cells, and the amplified 1.4-kb fragment was cloned into a pGEM-T-vector (Promega) to produce pT/hmina53 (465) and pT/hmina53 (464), encoding 465- and 464-amino acid proteins, respectively. The 1.4-kb HindIII-SalI fragment of pT/hmina53 (465) was extended and cloned using pGEFP-CS (Clonetech) cut with HindIII and SalI to produce pEGFP/hmina53 (465). The 1.4-kb HindIII-NotI fragment of pT/hmina53 (465) digested with HindIII and NotI was inserted into pRc/CMV (Invitrogen) to produce pmina53/Rc/CMV. The DNA fragment encoding human mina53 was amplified by PCR with 5'-GCCATGCCATGGCAAA-GAAAGCAAAGCCTAC-3' (SEQ ID NO: 6), adding NcoI site, and 5'-GGCATGCCATGGCTAGACTACTTGAAT-TAAAC-3' (SEQ ID NO: 7), adding NcoI site, as primers from pEGFP/hmina53 (465). The amplified 1.4-kb fragment was ligated with an E. coli expression vector pET11d (Novagen) cut with NcoI and de-phosphorylated with E. coli alkaline phosphatase to produce pET/hmina53. The 1.4-kb XhoI-SalI fragment, blunted with Klenow enzyme, of pEGFP/hmina53 (465) was inserted into pGEX-3X (Pharmacia), which was digested with EcoRI, blunted with Klenow enzyme, and de-phosphorylated with E. coli alkaline phosphatase to produce pGEX-hmina53.

Example 3

Reporter Plasmids Having a Mina53 Genomic DNA Fragment

A genomic DNA fragment of the human mina53 gene, which extends from the promoter region to part of intron 1, was amplified by PCR with 5'-CGGGATCCTGAACGCG- GAACACCGCCGGGTAGC-3' (SEQ ID NO: 8), adding a BamHI site, and 5'-CCCAAGCTTCCTCTTCCTC-CCAGTCTATCCTTC-3' (SEQ ID NO: 9), adding a HindIII site as primers using human peripheral blood derived DNA as a template. The 0.8-kb amplified fragment was cleaved with BamHI and HindIII and inserted into the 4.8-kb fragment of pGL3 (Promega) cut with BglII and HindIII followed by cutting with BamHI and HindIII to produce pMina(W)luci. pMina(W)luci was cleaved with HindIII and PmaCI, blunted with Klenow enzyme, and self-ligated to produce pMina(dE)luci. Mutation was introduced at E-box sites of pMina(W)luci using a Gene Editor™ in vitro site-directed mutagenesis system (Promega) to produce pMina (mE1)luci, pMina(mE2)luci, and pMina(mE1/2)luci, in which one or two E-boxes (CACGTG elements) were mutated to CACCTG.

Reference Example 1

Other Plasmids

The pActHyg plasmid, which contains a hygromycin resistance gene under control of an actin promoter, was a kind gift from Dr. M. Nakanishi (Tsuneoka, M. et al. (1997) Oncogene 14, 2301-2311). pRL-CMV plasmid, containing the *Renilla reniformis* luciferase gene under control of the CMV promoter was purchased from Promega.

Example 4

Preparation of RNA and Northern Blot Assay

RNA was isolated from cells by the acid guanidinium thiocyanate-phenol/chloroform extraction method using a DEPC-treated RNA preparation solution set (Nacalai tesque). The extracted RNA was electrophoresed in an agarose gel containing formaldehyde, transferred to Hybond-N™ membrane (Amersham Biosciences), and probed with $^{32}$P-labeled cDNA. Probes were labeled with [$\gamma$-$^{32}$P]dCTP using a Multiprime labeling kit (Amersham Biosciences). The results were quantified using a BAS200 image analyzer (Fuji Photo Film).

Example 5

Preparation of Probe DNAs

The DNA probes for c-myc, mina53, and CD18 were prepared as follows:
Preparation of c-Myc:
A 1.6-kb HindIII-XbaI fragment from pc-myc/CDM8 containing human c-myc cDNA was prepared (Tsuneoka, M., et al.: (1997) Oncogene 14, 2301-2311).
Preparation of Mina53:
A 442-bp fragment obtained by amplifying by means of PCR method with 5'-CAGAGCTGTCAACACCAGGTG-GAAAGTTAC-3' (SEQ ID NO: 10) and 5'-TGAATTCATC-CTCTCCTCGGCTCAGGTCTT-3' (SEQ ID NO: 5) as primers from pEGFP/hmina53 (465) as mentioned above, was used.
Preparation of CD18:
A 1.8-kb fragment amplified by RT-PCR method with 5'-GTTTGCCACTGATGACGGCTTCCATTC-3' (SEQ ID NO: 11) and 5'-AACACGCACCTAACCTCACCAACCT-CAA-3' (SEQ ID NO: 12) as primers from total RNA isolated from HL60 cells that had been cultured in 10 nM TPA for 24 hours. The sequence of CD18 cDNA was confirmed by direct sequencing method.

Example 6

Protocols on 5'-RACE and RT-RCR were explained as follows:
(Polymerase Chain Reaction (PCR))
Amplifications were performed in 50 μl of EX Taq™ DNA polymerase buffer containing 10 pmol of each primer, 1.2 units of EX Taq™ DNA polymerase (Takara Shuzo), and 200 μM dNTP.
(5'-RACE (Rapid Amplification of 5' cDNA Ends) Analysis)
Reverse transcriptase reaction, double-strand cDNA synthesis, and adapter ligation from poly(A)+ RNA (1 μg) of HEL cells were performed using a Marathon™ cDNA amplification kit (Clonetech) as described by Koda, Y. et al.: (1997) J. Biol. Chem. 272, 7501-7505. The first PCR was performed using as a primer, mina53-RACE-1 (5'-GCAG-TACTGTGAGGACAATGTGGTCTT-3' (SEQ ID NO: 13) and the AP1 primer. The temperature profile was initial denaturing at 94° C. for 1 minute followed by 25 cycles of denaturing at 96° C. for 15 seconds and annealing and extension at 68° C. for 3 minutes as one cycle. One μl of the first RACE-PCR product diluted 1000 times was used as the template for nest RACE-PCR. Nest RACE-PCR was performed using mina53-RACE-2 primer (5'-CAACCAAG-GAGCCAAAGTAACATTC-3' (SEQ ID NO: 14)) and the AP2 primer. The temperature profile was initial denaturing at 94° C. for 1 minute followed by 25 cycles of denaturing at 96° C. for 15 seconds and annealing and extension at 68° C. for 4 minutes as one cycle.

(RT-PCR (Reverse Transcriptase-PCR))
The single-strand cDNA of human HEL or RCN-9 cells, or mouse gastric cells were synthesized on total RNA (1 μg) using commercially available Superscript™ single-strand cDNA synthesis kit (Invitrogen). One μl (total 20 μl) of resultant single-strand cDNA was used as the template for PCR. The RT-PCR primers for the amplification were mina53 RT-F (5'-ACACCGGTGACGAGCGCACG-GAAAG-3' (SEQ ID NO: 15)) and mina53 RT-R (5'-GC-CTCTCATCTGTGGGGAAGTATTA-3' (SEQ ID NO: 16)) for human and rat mina53 RT-F (5'-TTTCCTCCCTACT-TGTGAACAATGC-3' (SEQ ID NO: 17)) and rat mina53 RT-R (5'-AATGATGCTCTTTAAAGGAGTTATTT-3' (SEQ ID NO: 18)) for rat and mouse. The temperature profile was 35 cycles of denaturing at 98° C. for 15 seconds, annealing at 65° C. for 1 minute, and extension at 72° C. for 2.5 minutes as one cycle.

Example 7

Cell Culture

Human glioblastoma cell line T98G cells were cultured in Eagle's medium supplemented with nonessential amino acids and 10% fetal calf serum (FCS). HeLa cells, rat fibroblast cell line 3Y1 and its derivatives were cultured in Dulbecco's modified Eagle's medium supplemented with 10% FCS. Human promyelocytic leukemia HL60 cells were cultured in RPMI 1640 medium supplemented with 20% FCS. Rat colon cancer cell line RCN-9 was obtained from Riken Cell Bank and cultured in RPMI 1640 medium supplemented with 10% FCS. To establish 3Y1 cells expressing c-Myc or mutant c-Myc lacking a large part of transcriptional activation domain, cells were transfected with 0.4 µg of pActHyg and 20 µg of pc-myc/CDM8 or pc-myc(d41-178)/CDM9 by a calcium phosphate method (Chen, C. A., et al.: (1988) Biotechniques 6, 632-638). Transfected cells were cultured for 2 weeks in the medium containing 200 µg/ml hygromycin. Individual clones were isolated, and the expression of c-Myc or mutant c-Myc protein was detected by Western blot analysis using anti-c-Myc antibody. Clones 3Y1MycA and 3Y1MycB (expressing c-Myc protein) and 3Y1Myc(dTAD)A and 3Y1Myc(dTAD)B (expressing mutant c-Myc protein lacking the transcriptional activation domain) were established. To establish human glioblastoma T98G cells expressing c-MycER chimeric protein (T98Gmycer-2 cells), cells were transfected with 20 µg of pc-mycer/CAGGS and 0.4 µg of pActHyg, and the expression of c-MycER in individual clones was detected as described above.

Example 8

Differential Display Using DNA Chip cDNA Micro Array

Total RNA from untreated T98Gmycer-2 cells and from cells treated by OHT for 20 hours was isolated. Poly(A+) RNA was recovered and subjected to differential display using a commercially available DNA chip (Incyte Genomics). About 9000 kinds of cDNAs including expressed sequence tag (EST) clones were plated on the chip (Uni-GEM Human V Ver. 2).

Example 9

Transient Expression Assay

T98Gmycer-2 cells were grown in medium supplemented with 10% FCS. $3 \times 10^4$ cells were plated into a dish (12-well plate; well diameter, 22 mm) and cultured for 20-24 hours. Transfections were carried out using FuGENE 6™ transfection reagent (Roche Diagnostics) with 1 µg of the reporter plasmids and 20 ng of pRL-CMV as an internal transfection marker. One day after transfection, OHT (final concentration, 0.2 µM) was added to activate MycER chimeric protein, and cells were further cultured for 17 hours. Cells were then collected and analyzed for firefly luciferase and *Renilla reniformis* luciferase activities using a Dual luciferase reporter assay system (Promega). After normalization of the degree of gene transfection among the samples by using *Renilla reniformis* luciferase activities, firefly luciferase activities from cells with activated c-MycER were expressed as the ratio of activities from cells without the MycER activation. To normalize the effect of OHT not through MycER activation, the values from T98Gmycer-2 cells were divided by the values from T98G parent cells treated with the same method as the above T98Gmycer-2 cells to obtain the reactivities of reporter genes to the activation of MycER chimeric protein. Each value is represented as a mean of 4 time experiments.

Example 10

Chromatin Immunoprecipitation

Chromatin immunoprecipitation assay was performed by using antibodies for c-Myc and control antibodies, and control experiments without antibodies were also carried out. In these experiments, two kinds of antibodies for c-Myc were used. One was that react with half site of N-terminal of c-Myc and other is that mainly binds with the half site of C-terminal. Assay was principally carried out according to the methods already published (Boyd, K. E., et al.: (1977) Mol. Cell. Biol., 17, 2529-2537). Immune complexes were recovered by adding 20 µl of protein A beads treated to prevent the nonspecific binding. As the same procedures described in the above-mentioned publication, the beads were washed, the DNA fragments were eluted, and the eluted solutions were extracted with phenol/chloroform and precipitated with ethanol. Then, immunoprecipitated DNA fragments were detected by PCR. PCR primers were 5'-GC-CGGCGCTGTGGTTGCGGGACCTG-3' (SEQ ID NO: 19) and 5'-TCCTCTTCCTCCCAGTCTATCCTTC-3' (SEQ ID NO: 20), which were used to amplify a 483-bp fragment containing E-boxes near the transcription initiation sites of the human mina53 gene. As other primer, 5'-TTACAGG-TAAGCCCTCCAATGACC-3' (SEQ ID NO: 21) and 5'-GCAAAGCTACCATTTAGGAACCC-3' (SEQ ID NO: 22) were used to amplify the genomic sequence of a region containing an E-box located in the region without detectable gene (Bouchard, C., et al.: (2001) Genes & Dev., 15, 2042-2047) of chromosome 22. This E-box is located in a chromosomal region without any detectable genes (Bouchard, C., et al.: (2001) Genes & Dev., 15, 2042-2047).

Example 11

Antibodies

Human mina53 (from the third amino acid Lys to the carboxyl-terminal end) was expressed using pET/hmina53 in commercially available *E. coli* BL21(DE3) (Novagen) and isolated and purified by SDS-PAGE. Rabbits were immunized with the recombinant polypeptide. The GST-fusion protein, GST-Mina53 was expressed using pGEX-hmina53 in *E. coli* JM109 and isolated by a glutathione-Sepharose™ column (Pharmacia). Polyclonal anti-Mina53 antibody was purified from rabbit serum using Sepharose™ 4B (agarose bead) conjugated with recombinant GST-Mina53 polypeptide as described in the publication mentioned above. One anti-c-Myc antibody used was that was previously reported.

Reference Example 2

Other antibodies used were commercially available. As the other antibodies, there included anti-c-Myc antibody (N262) (Santa Cruz Biotechnology), mouse anti-nucleolin monoclonal antibody (C23) (Santa Cruz Biotechnology), goat anti-rabbit IgG-HRP antibody (Santa Cruz Biotechnology), Alexa 488-conjugated anti-mouse IgG (Molecular Probes), Cys-conjugated anti-rabbit IgG (Zymed Laboratories).

Example 12

Western Blot Analysis and Indirect Immunofluorescence Staining

Western blot analysis was performed using the same procedures as described in the above mentioned publication (Tsuneoka, M., et al.: (1988) J. Biochem. 104, 560-564). Cells were trypsinized and extracted in 3% SDS solution containing 100 mM Tris (pH 6.8), 0.1 M DTT and 20% glycerol. Cell extracts were separated on 4-20% polyacrylamide gels and transferred to a polyvinylidene difluoride (PVDF) Millipore membrane (Millipore). After treatment with antibodies, signals were detected using an ECL enhanced chemiluminescence technique (Amersham Pharmacia).

For indirect immunofluoresence staining, HeLa cells grown on glass coverslips in a 6-well plate were fixed in methanol for 10 minutes at 20° C. Anti-Mina53 rabbit antibody and mouse anti-nucleolin monoclonal antibody were added and incubated for 120 minutes at 37° C. After washing in a suspension of 0.1% skim milk in PBS three times, Alexa 488-conjugated anti-mouse IgG and Cy3-conjugated anti-rabbit IgG were added, incubated for 120 minutes at 37° C., and washed with a suspension of 0.1% skim milk in PBS three times. Finally, cells were embedded in Immunon (Thermo Shandon) and observed under a fluorescence microscope.

Example 13

Preparation of RNA and Introduction of siRNA into Cells

It has been recently published that the double-strand chain of small interfering RNA (siRNA) comprising 21 nucleotides specifically inhibit the gene expression in the mammalian cell lines inclusive of HeLa cell (Elbashir, S. M., et al.: (2001) Nature 411, 494-498). Then, siRNA double-helix comprising 21 nucleotides and being specific to human mina53 and rat mina53 (5 nucleotides in the 19 nucleotides are different from human ones) was chemically synthesized according to the conventional method. As nonspecific control, double-strand having an inverted sequence of the human mina53 siRNA was used. The siRNA sequences targeting human Mina53 and rat Mina53 were in positions 45-63 relative to the first nucleotide of the initial codon and the two-nucleotide 3' overhang of deoxythymidine. The siRNAs were annealed and transfected essentially as described in the publication (Elbashir, S. M., et al.: (2001) Nature 411, 494-498). Twenty-four hours before transfection by siRNA, cells in an exponentially growing phase were trypsinized and transferred to a 12-well plate. Transfection of siRNA was carried out with 200 pmol of siRNA per well using Oligofectamine™ transfection reagent (Life Technology), provided that HeLa cells were cultured for 20 hours for transfection in a non-serum medium, and 3Y1MycB cells were cultured for 10 hours in a similar manner.

Example 14

Preparation of Anti-Human Mina53 Monoclonal Antibody

Antigen

Recombinant human Mina53 protein was prepared in *E. coli*. A solution of antigen for sensitization was prepared by mixing the isolated protein with an MPL+TDM adjuvant (Sigma)

Schedule for Immunization

Each paw of the hind limb of 8-10 week-old BALB/c mice was injected 0.1 ml (0.5 mg/ml, Mina53 protein). The total amount per one immunization was 0.2 ml of the above mentioned solution of antigen. After the first injection, the antigen was injected in a similar manner on the third day and the sixth day. After 14 days, an antigen without mixing the adjuvant was injected at the same amount as above and in a similar manner as above and boosted.

Recovery of B Cell

On the fourth day after the final boost, lymphocytes were isolated from lymph nodes of the hind limb under aseptic condition and B cells were recovered by mashing and breaking the lymph nodes with two pieces of sterilized slide glasses.

Cell Fusion

After mixing the recovered B cells with mouse F01 myeloma cells at the ratio of 10:1, cell fusion was performed by using polyethylene glycol (PEG) 4000.

Selection of Hybridoma

The fused cells were cultured in 96-well plates. By using RPM1 1640 medium supplemented with 5% Briclone™ (Dainippon Pharmaceuticals Co.), 20% fetal calf serum and HAT solution as the medium, the mouse myeloma cells fused with B cells (hybridoma) were selectively survived. In the cultivation, non-fused thymus cells were used together to aid the growth of hybridoma.

As performed above, four hybridomas were selected and one of the hybridomas (mouse-mouse hybridoma MT/HK-1) was deposited in International Patent Organisms Depositary, National Institute of Advanced Industrial Science and Technology (Central 6, 1-1-1 Higashi, Tsukuba, Ibaraki, Japan) under FERM P-19298 on Apr. 9, 2003.

Example 15

Method for Measuring the Activity of Anti-Mina53 Monoclonal Antibody

The purified recombinant human protein Mina53 was added to a solution of 10 mM Tris (pH8.0) to obtain a solution of 3 to 10 g/ml of the protein. 0.1 ml of the obtained solution was plated in each well of micro-titer plates and kept for 3 hours to overnight at room temperature left. Thereafter, the solution in each well was discarded, 0.2 ml of a solution containing 1% skim milk in PBS (phosphate buffered saline) was added, and the solution was maintained at 4° C. (blocking operation). Plates were used in 2 hours to a week. After 1% skim milk solution was discarded, wells were washed with PBS twice and to the well 0.1 ml of the solution for assay was added and incubation was carried out at 37° C. for 2 hours or at 4° C. for overnight. After the wells were washed with PBS three times, 0.1 ml solution of horseradish peroxidase-conjugated anti-mouse IgG was added and then incubation was conducted at 37° C. for 2 hours or at 4° C. for overnight. After the wells were washed with PBS three times, 0.1 ml of o-PDA solution (0.1 M citrate solution of 0.4 mg/ml o-phenylenediamine, 0.2M $Na_2HPO_4$, 0.005% $H_2O_2$) was added, and the solution was kept at room temperature for 15 minutes to 30 minutes left and then the reaction made stopped by adding 0.05 ml of oxalate solution. The activity of peroxidase was measured by measuring the absorption at 450 nm.

The activity of anti-Mina53 antibody in the above-mentioned hybridoma cultured medium was measured by sampling 0.1 ml of the culture medium on the 14th day and 21st day after culture and measuring such sample by the above-mentioned method.

Example 16

Western Blotting

HeLa cells were extracted with SDS solution (3% SDS, 0.125 M Tris-HCl (pH 6.8), 20 mM dithiothreitol, and 20% glycerol) at 100° C. for 10 minutes, subjected to SDS-PAGE and transferred to a polyvinylidene difluoride microporous membrane (Millipore, Bedford, Mass.). The membrane was incubated with the hybridoma culture medium at 37° C. for 30 minutes and washed and further incubated with horse-radish-peroxidase-conjugated anti-mouse IgG solution at 37° C. for 30 minutes and then washed again. The signal was detected by commercially available enhanced chemiluminescence technique (Amersham Bioscience) system and Western blotting analysis was performed.

Example 17

Purification of Anti-Mina53 Monoclonal Antibody

To mice (balb/c) to which pristane (2,6,10,14-tetramethylpentadecane) was intraperitoneally injected in advance before about 2 week was intraperitoneally injected the above-mentioned hybridoma ($2 \times 10^6$/mouse). After 10 to 20 days, ascites were recovered by using 18-gauge injection needle. The ascites were fractionized with ammonium sulfate and the fractions exhibiting antibody activity were dialyzed against 10 mM Tris(pH8.0) solution. To DE-52 (Whatman) in equilibrium with 10 mM Tris (pH8.0) in advance were added the above-mentioned fractions and the eluent fractions were eluted with 10 mM Tris (pH8.0) containing 0 to 0.2 mM sodium chloride in gradient concentration, and the activity of anti-Mina53 antibody was measured in the each eluted fraction. The fractions exhibiting the high activity of anti-Mina53 antibody were collected and purified to attain the purified anti-Mina53 monoclonal antibody.

Example 18

Diagnosis of Tissue by Using Anti-Human Mina53 Monoclonal Antibody

Using anti-human Mina53 mouse anti-Mina53 monoclonal antibody stained the colon cancers. As a result, colon cancer regions were strongly stained compared with non-neoplastic tissues.

(Histostaining by Anti-Human Mina53 Mouse Anti-Mina53 Monoclonal Antibody)

Formalin-fixed and paraffin-embedded block was sliced to about 3 μm in thickness and mounted on slide glass. The sections on the slide glass were immersed in xylene and maintained at 37° C. for 15 minutes. After 15 minutes, solvent was replaced with new xylene. This treatment with xylene was repeated three times to perform de-paraffinized treatment. The sections thus de-paraffinized were immersed in 99% ethanol and the ethanol was replaced with new ethanol. After the treatment with ethanol was repeated three times in total, the sections were immersed to 95%, 90% and then 70% ethanol having gradiently high water contents for 5 minutes, respectively. Further, the sections were immersed to water for 5 minutes to wash. The sections which were washed with water were subjected to autoclave in 10 mM citrate buffer solution (pH6.0) at 121° C. for 20 minutes to recover the antigenicity. Then, the temperature returned to room temperature and the obtained sections were washed with water and then immersed in PBS solution.

Then, the sections were washed once with PBS solution containing 0.05% Tween20, and the specimens were treated with a solution of 3% $H_2O_2$ in PBS at room temperature for 30 minutes to inactivate the endogenous peroxidase activity.

The specimens obtained were washed with a PBS solution containing 0.05% Tween 20 twice, and treated with a PBS solution containing 1% skim milk and 5% rabbit serum at room temperature for 30 minutes to perform the blocking operation for inhibiting the nonspecific binding of antibody.

Final concentration of the antibody was adjusted to 3.5 μg/ml by diluting with a PBS solution containing 1% skim milk and such antibody put on the specimens obtained by the above-mentioned blocking operation on the side glass and then reacted at 4° C. overnight. Then, the specimens was washed three times with PBS solution containing 0.05% Tween 20 and incubated with a biotinylated rabbit anti-mouse IgG antibody at room temperature for 30 minutes.

After incubation, the obtained specimens were washed three times with PBS solution containing 0.05% Tween 20 and then incubated with horse radish peroxidase conjugated streptavidin. The specimens obtained was washed with PBS solution containing 0.05% Tween 20 three times and then 3,3-diaminobenzidine(DAB) substrate solution was added and the mixture kept left at room temperature to develop the color of the part having peroxidase activity to brown. Then, washing for 4 minutes with water stopped the peroxidase reaction. After staining with hematoxylin, slide glass was dehydrated and embedded.

Example 19

Quantitative Analysis of Mina53 Protein in a Solution Using Anti-Human Mina53 Monoclonal Antibody The sandwich-combination of two anti-human Mina53 monoclonal antibodies achieved to carry out the quantitative analysis of Mina53 protein.

(Quantitative Analysis of Mina53 by Micro-Titer Plates)

The anti-Mina53 monoclonal antibody was labeled with horse radish peroxidase binding kit (Alpha Diagnostic International, San Antonio, Tex., USA) according to the instruction of kit to prepare anti-Mina53 monoclonal antibody bound with horse radish peroxidase.

Further, o-phenylenediamine solution was prepared by dissolving o-PDA (at the concentration of 0.4 mg/ml) in a solution of 0.1M citrate/0.2M $Na_2HPO_4$, storing at −80° C., and adding one thousandth volume of aqueous solution of 5% hydrogen peroxide just before using.

On the other hand, 20 μg/ml of another antibody was dissolved in 10 mM Tris (pH6.8) and 50 μl of the solution was added to each well of the micro-titer plates and then incubated at 37° C. for 2 hours or at 4° C. overnight. Then, after disregarding the antibody solution, 200 μl of PBS solution containing 1% skim milk was added and incubated at 37° C. for 2 hours or at 4° C. overnight. Then, 50 μl each of the specimens was added per well, and incubated at 37° C. for 2 hours or at 4° C. overnight. If necessary, the specimens were diluted with fetal calf serum. After washing with PBS three times, each 50 μl of diluted antibody solution bound with horse radish peroxidase as mentioned above was added per well and then incubated at 37° C. for 2 hours or at 4° C. overnight. Furthermore, after washing with PBS three times, each 50 μl of o-phenylenediamine solution was added per well and then incubated at 37° C. for 2 hours or at 4° C. overnight to measure the coloration.

Example 20

Western Blotting

For Western blotting analysis, human colon cancer cell lines HT-29, SW-620 and WiDr were cultured in Dulbecco's modified Eagle's medium containing 10% FCS, respectively and human promyelocytic leukemia cell line HL60 was cultured in RPMI1640 medium containing 10% FCS.

The cells thus cultured were collected by the treatment with a PBS buffer (PBS) containing trypsin and EDTA and washed with PBS. Cells were then suspended in 0.125 M Tris-HCl buffer (pH 6.8) containing 3% SDS, 50 mM dithiothreitol, and 20% glycerol and boiled for 10 minutes prior to separation on a gradient SDS-polyacrylamide gel (4-20%). Proteins were transferred to a polyvinylidene difluoride microporous membrane, and nonspecific binding sites were blocked with PBS solution containing 1% skim milk. After treatment with mouse monoclonal anti-Mina53 monoclonal antibody and HRP-conjugated goat anti-mouse IgG antibody, signals were detected using an enhanced chemiluminescence (ECL) Western blotting detection reagent system. As the loading control, the membrane was re-probed with a monoclonal anti-β-actin monoclonal antibody after treatment with a stripping buffer.

FIG. 6A shows the results of Western blotting analysis. Western blotting was carried out by electrophoresing the cell lysates prepared from HL60 cells cultured in the absence of TPA (lane 1), HL60 cells cultured in the presence of TPA (lane 2), and colon cancer cell lines WiDr (lane 3), HT-90 (lane 4) and SW-620 (lane 5) and using anti-Mina53 monoclonal antibody (upper panel).

Indirect Immunofluorescence Staining

For indirect immunofluorescence staining, HT-29, SW620 and WiDr cells grown on glass coverslips of six-well plates were fixed in methanol for 10 minutes at −20° C. After blocking the coverslips with PBS solution containing 1% skim milk, mouse anti-Mina53 monoclonal and rabbit anti-nucleolin polyclonal antibodies were added thereto and incubated for 120 minutes at 37° C. After washing with PBS solution containing 0.1% skim milk three times, Alexa 488-conjugated anti-mouse IgG and Cy3-conjugated anti-rabbit IgG antibodies were added thereto, incubated for 120 minutes at 37° C. and washed three times with PBS solution containing 0.1% skim milk. Finally, cells were embedded in Immunon and observed with a fluorescence microscope.

Figure 6:
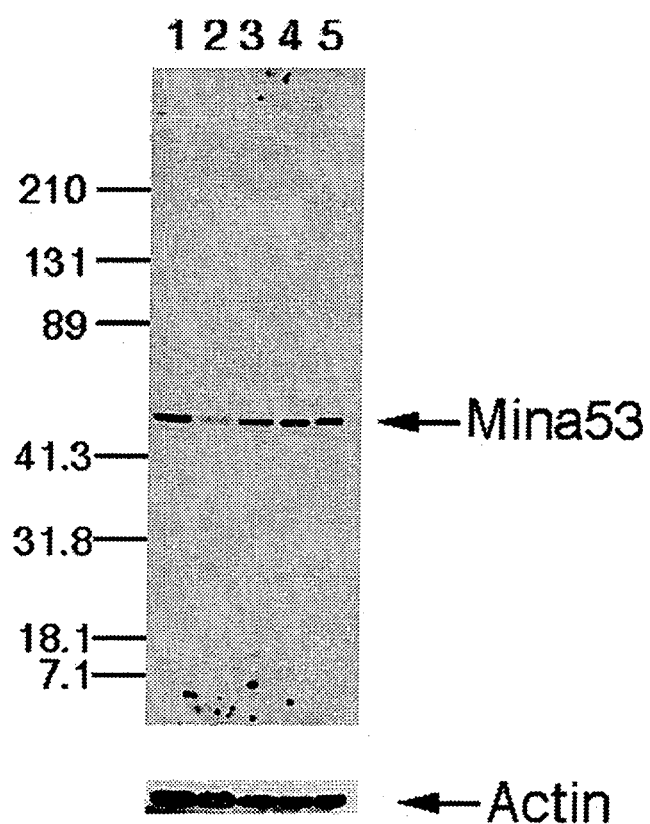
FIG. 6A shows the results of Western blotting analysis on Mina53 protein using anti-Mina53 monoclonal antibody.
FIG. 6B shows the intracellular localized states.
Figure 6:
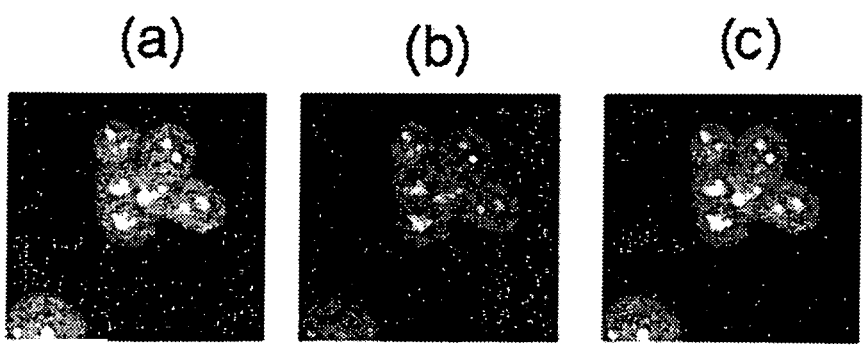

FIG. 6B shows the subcellular localization of Mina53 protein. In FIG. 6, the localization of Mina53 protein in colon cancer cell line SW-620 was visually observed by indirect immunofluorescence staining (a). Staining with anti-nucleorin rabbit polyclonal antibody was visually observed (b). Further, an overlapped image is shown (c).

Example 21

The formalin-fixed and paraffin-embedded specimens from 24 patients with primary colon neoplasia were used (Fujitani N, et al.: Glycoconjugate J 2000, 17: 331-338). The specimens included 23 cases of adenocarcinoma of the colon, in some of which tumor cells had invaded deeply into non-neoplastic tissues or into lymphatic vessels. There was also one case of adenoma. Tissue sections were classified after hematoxylin and eosin (HE) staining according to the pathological grading system as well, moderately, and poorly differentiated. The characteristics of the tissues are outlined in Table 1.

Example 22

Immunostaining of Colon Tumor Tissues

De-paraffinized sections of 10% formalin-fixed, paraffin-embedded colon tumor tissues were immunostained by the streptavidin-biotin complex immunoperoxidase method (Fujitani, N., et al: J Histochem Cytochem 2000, 48: 1649-1656).

Sections mounted on slides were autoclaved for 20 minutes in 10 mM sodium citrate buffer (pH 6.0) for antigen retrieval. After pretreatment with 3% $H_2O_2$ in PBS and then with 1% skim milk and 5% rabbit serum in PBS, the antibody against Mina53 at a final concentration of 3.5 μg/ml in 1% skim milk or anti-Ki-67 antibody was reacted overnight at 4° C. in a moist chamber. After 3 washes with 0.05% Tween 20 in PBS, sections were incubated sequentially with biotinylated rabbit anti-mouse IgG and then with HRP-streptavidin conjugate. Color was developed with 3,3-diaminobenzidine and $H_2O_2$ for 4 (Mina53) or 2 (Ki-67) minutes and then rinsed with water to stop the reaction. After light counterstaining with hematoxylin, the slides were dehydrated, coverslipped, and observed with a microscope.

Evaluation of Immunohistochemical Staining

Each section was scored on a scale from 0 to 3 by visual observation of the staining intensity shown in Table 1 mentioned below. The highest staining intensity was scored as 3, the lowest as 1 and no staining at all as 0. For estimation of the percentage of stained cells, images were captured with a digital camera. The number of positive cells within representative fields were counted and expressed as the percentage of cells stained. The staining index in the under mentioned Table 1 was calculated as staining intensity multiplied by the average percentage of cells stained.

Example 23

Quantitative Analysis of Recombinant Human Protein Mina53

Figure 10:
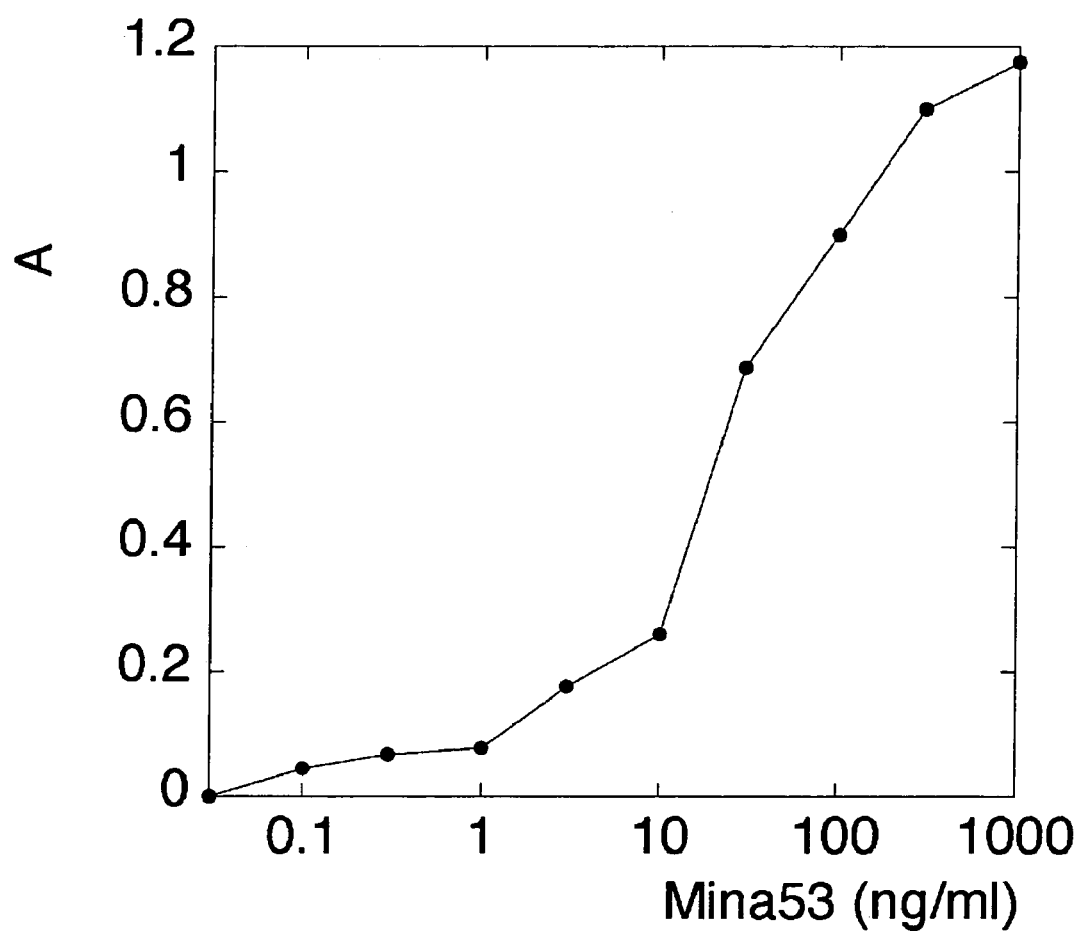
FIG. 10 shows the graph for the detecting curve of recombinant Mina53 protein.

The recombinant human protein Mina53 produced by *E. coli* was added to fetal calf serum to obtain a solution of 0.1 to 1000 ng/ml of the protein, and quantitatively assayed by ELIZA method. As a result, 1 to 1000 ng/ml recombinant human protein Mina53 could be quantitatively analyzed (FIG. 10).

Example 24

Figure 11:
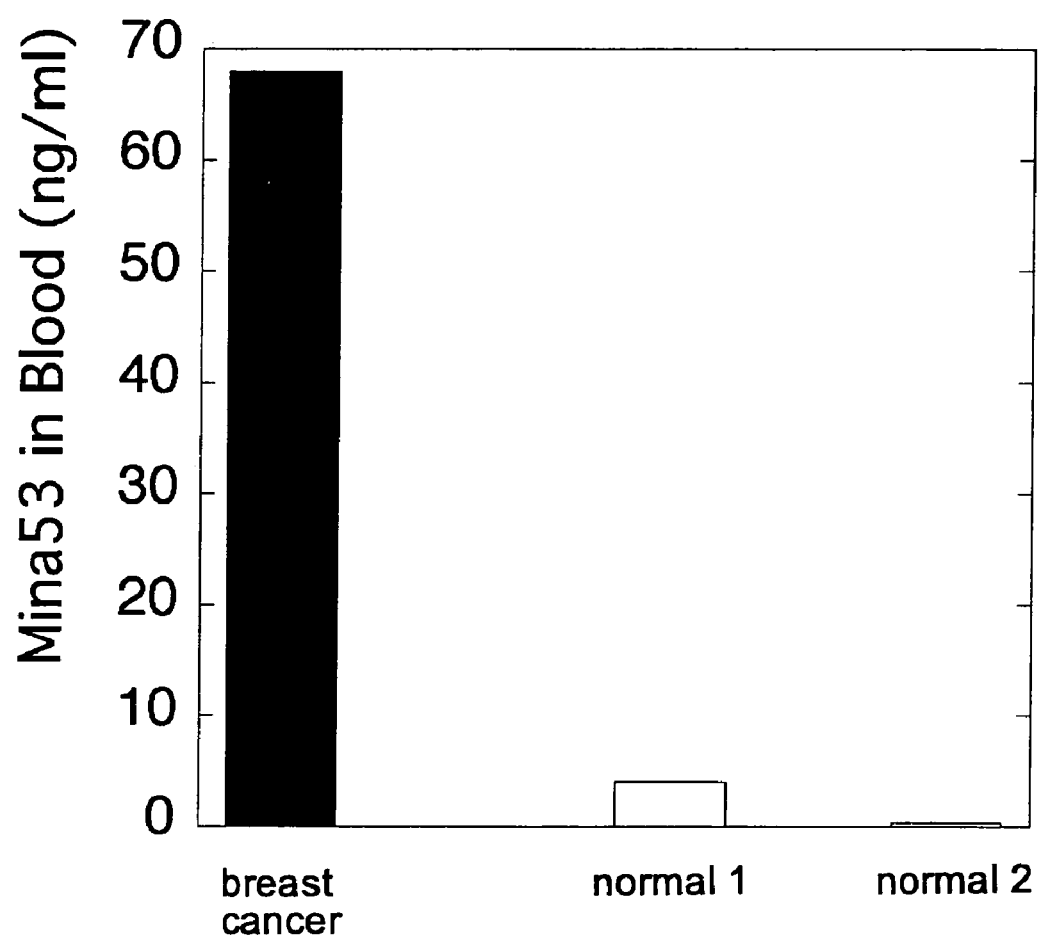
FIG. 11 shows the graph for amount of Mina53 protein in human blood.

The amount of Mina53 in the blood of normal person was analyzed according to the method described in Example 23 to detect 0 to 5 ng/ml of Mina53. In the blood of the patient suffered from mammary cancer, 64 ng/ml of Mina 53, higher level than the normal value was detected (FIG. 11).

The above example illustrates that Mina53 in the blood can be quantitatively analyzed according to ELIZA method.

Example 25

Staining of Esophageal Cell Carcinoma

Esophageal cell carcinomas were stained with the anti-Mina53 monoclonal antibody obtained in the above example and the degree of staining was compared to the staining of esophageal cell carcinoma by anti-Ki-67 monoclonal antibody currently used for the staining of esophageal cell carcinoma.

Figure 13:
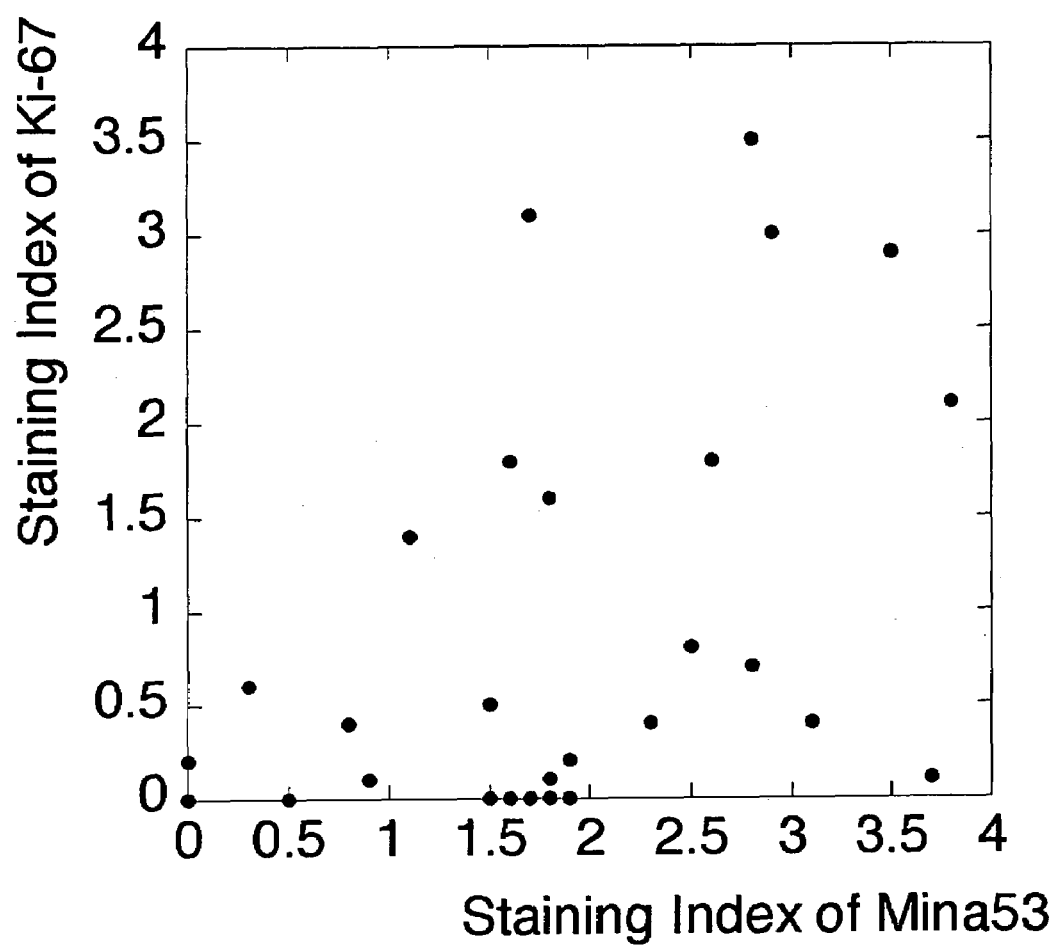
FIG. 13 shows the comparison of the degree of expression of Mina53 and Ki-67 against esophageal cancer tissues.

The esophageal carcinoma tissues from 38 patients suffered from esophageal carcinoma were stained with anti-Mina53 monoclonal antibody or anti-Ki-67 monoclonal antibody and staining indexes of anti-Mina53 monoclonal antibody or anti-Ki-67 monoclonal antibody in each sample were determined. In this example, the staining index for anti-Mina53 monoclonal antibody is expressed on the y-axis, and the staining index for anti-Ki-67 monoclonal antibody is expressed on the x-axis, and the values of each esophageal carcinoma tissues are plotted. The staining indexes were determined by multiplying staining intensity with the ratio of stained cells. The results are shown in FIG. 13.

Figure 12:
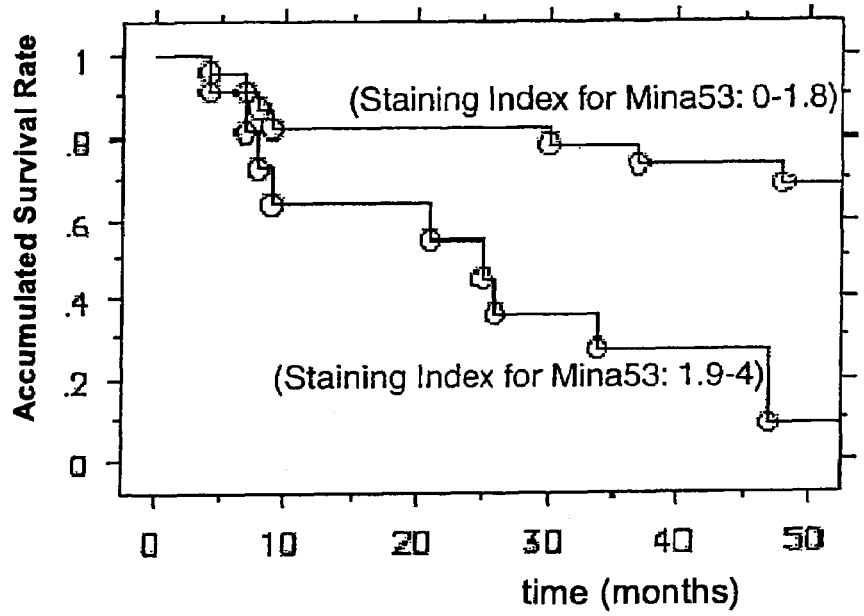
FIG. 12 shows the relationship between Mina53 and Ki-67 expression and survival rate. (A) shows the relationship between the expression and survival rate of Mina53, and (B) shows the relationship between the expression and survival rate of Ki-67.
Figure 12:
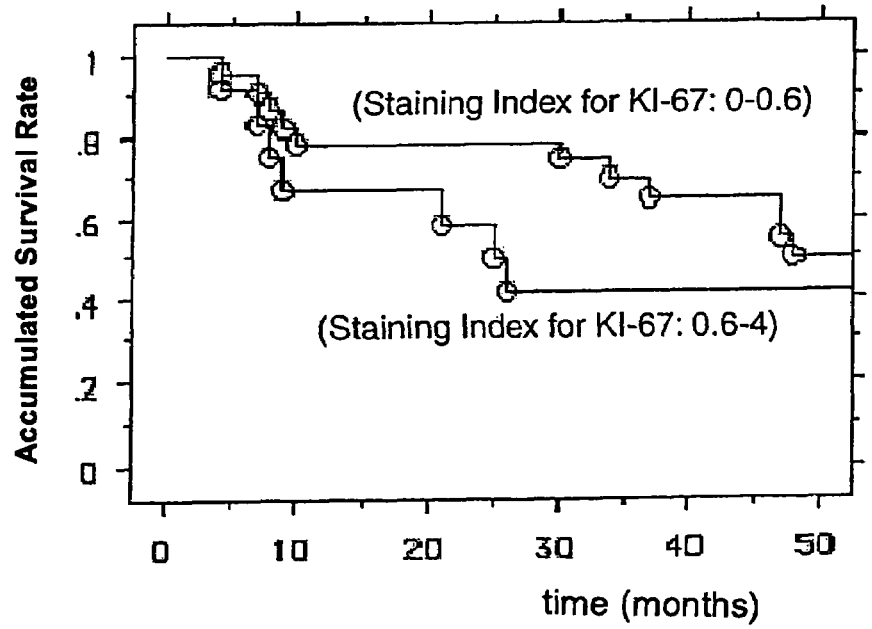

The relationship between the malignancy of esophageal carcinoma and staining indexes for Mina53 or Ki-67 was examined and the results are shown in FIG. 12. FIG. 12(A) shows the relationship between the staining index for Mina53 and the malignancy of esophageal carcinoma and FIG. 12(B) shows the relationship between the staining index for Ki-67 and the malignancy of esophageal carcinoma. In FIG. 12(A), the results divided into two classes with 0-1.8 and 1.9-4 Mina53 staining indexes according to Kaplan-Meier method are shown. In FIG. 12(B), the results are divided into two classes with 0-0.6 and 0.7-4.0 Ki-67 staining index according to Kaplan-Meier method.

Results

In the above examples, to conditionally activate c-Myc activity, the estrogen-inducible Myc system was used (Eilers, M., et al.: (1989) Nature 340, 66-68). The chimeric protein c-MycER consists of human c-Myc and the estrogen binding domain of the human estrogen receptor. c-MycER anchors to cytoskeletal components of cells in the absence of estrogen. When estrogen or its derivative, 4-hydroxytamoxifen (OHT), binds to the chimeric protein, it becomes free from cytoskeleton to function as c-Myc. The human glioblastoma cell line T98G was used as the parental cells into which ectopic c-Myc activity was introduced. A T98G cell line expressing c-MycER protein (T98Gmycer-2 cells) was established.

Cells in an exponentially growing phase were cultured in the presence or absence of OHT for 20 hours and total RNAs were isolated, and subjected to the above mentioned cDNA micro array analysis. Specific signals for Myc target genes, ODC and nucleolin which were already reported, were increased by 2.6- and 1.6-fold accompanied with the activity of c-MycER, respectively. These results suggest that Myc target genes could be detected in this experimental system.

In the above examples, human EST sequences among genes stimulated by c-MycER activation and highly expressed were investigated for the elucidation of the c-Myc functions. The result indicated that the signal for EST clone W27666 was stimulated by 1.9-fold with c-Myc activation. This stimulation rate is similar to those of the Myc-targeted genes, ODC and nucleolin, measured in this invention.

cDNA encoding the 5' upstream part of EST clone W27666 was isolated using the 5'-RACE protocol from a library of human erythroid leukemia: HEL cells. Two kinds of cDNAs with different sequences at the 5' terminus were also isolated. From the results of the nucleotide sequences from 5'-RACE experiments and EST having nucleotide sequence consistent with those of EST clone W27666, the whole sequence of the mRNA molecule was predicted. Using primers consistent with 5'-part and 3'-part sequences of the predicted molecule, a 2,3-kb-length cDNA was amplified by RT-PCR protocol. The amplified cDNA was cloned into a vector and sequenced. The majority of obtained cDNA clones encode a protein of 465 amino acids with a predicted molecular weight of 52,800.28 Da (SEQ ID NO: 1 in Sequence Listing).

The subcellular localization of this protein was visualized by indirect immunofluorescence staining with the specific antibody. It has become apparent that this protein is localized in the nucleus. In addition to the diffuse localization in the nucleus, strong dotted staining was observed within the nucleus. Double staining with anti-nucleolin antibody indicated that these dots were consistent with nucleoli. Nuclear and nucleolar localization was also observed when GFP-Mina53 fusion protein was expressed. These results suggest that Mina53 is a nuclear protein localized in nucleoplasma and nucleoli.

The cDNA encoding a 464-amino acid protein with a predicted molecular weight of 52,672.15 Da was also cloned. This protein lacks Gln-297 of the major protein. A cDNA having 101 bp inserted in the middle part of the mina53 cDNA was also detected. There is a stop codon in the inserted sequence, and the cDNA encodes 1 to 262 amino acids of Mina53 protein and 18 novel amino acids. Although the amount of this mRNA was small, this mRNA molecule in cDNA libraries made from a human erythroid leukemia cell line (HEL), a human ovary mucinous cystadenocarcinoma cell line (MCAS) and a human colon adenocarcinoma cell line (WiDr) was detected.

As the result of the study that Mina53 was conserved in human, rat and mouse, a mouse cDNA that appeared to be an orthologue of human mina53 was found by a Blast search (GenBankAcc: NM_025910). Based on this sequence, mouse mina53 cDNA was isolated according to an RT-PCR protocol. The isolated sequence was different from the nucleotide sequence of GenBankAcc: NM_025910 and two amino acids in the amino acid sequence are different (SEQ ID NO: 2 of the Sequence Listing). A rat EST (GenBankAcc: H32933) that is 300 bp in length and is homologous to the 3'-untranslated region of mouse and human mina53 was also found. Using primers that were predicted to amplify rat mina53 mRNA, rat mina53 cDNA from RCN-9 cells was isolated according to an RT-PCR protocol (SEQ ID NO: 3 of the Sequence Listing). The open reading frame (ORF) of rat and mouse mina53 encodes 465 amino acid proteins. Rat and mouse amino acid sequences of Mina53 proteins were 86% identical to each other, those of human and mouse were 72% identical, and those of human and rat were 75% identical, suggesting that mina53 is conserved in mammals. A nucleotide 3 bp upstream of the methionine initiation codon is A in mina53 of all the three species, conforming to a Kozak consensus sequence. Rat mina53 gene and mouse mina53 gene as well as human mina53 gene are useful for the elucidation of the mechanism of cell proliferation and are useful for the research of cancer cell diagnostic methods.

Figure 2:
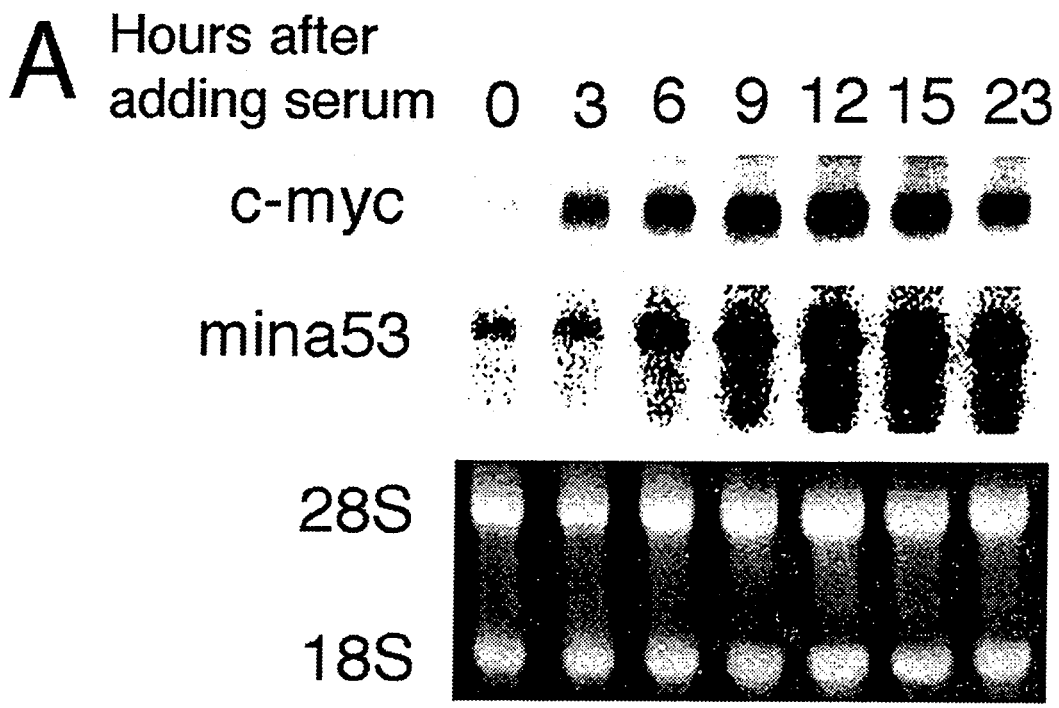
FIG. 2 shows the expression level of mina53 mRNA.
Figure 2:
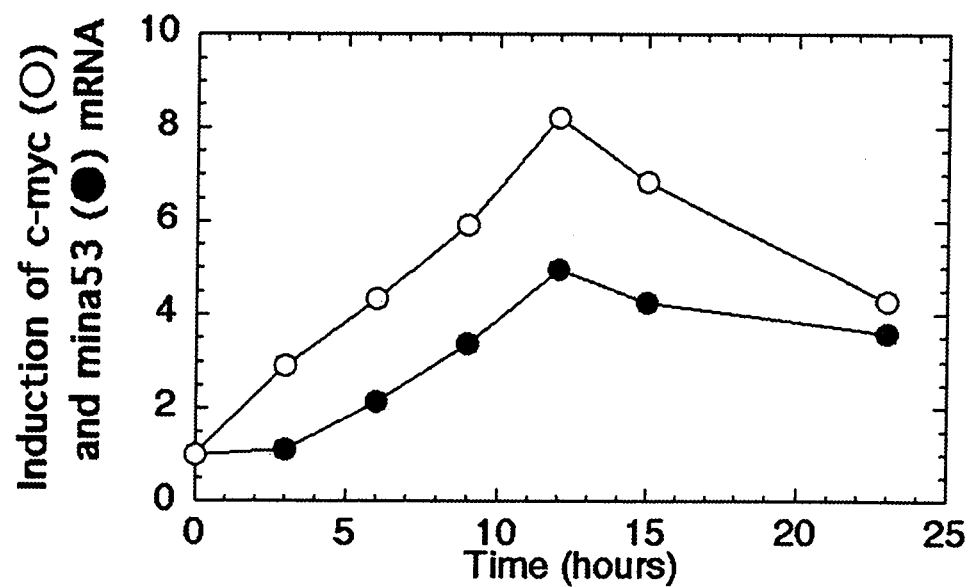
Figure 2:
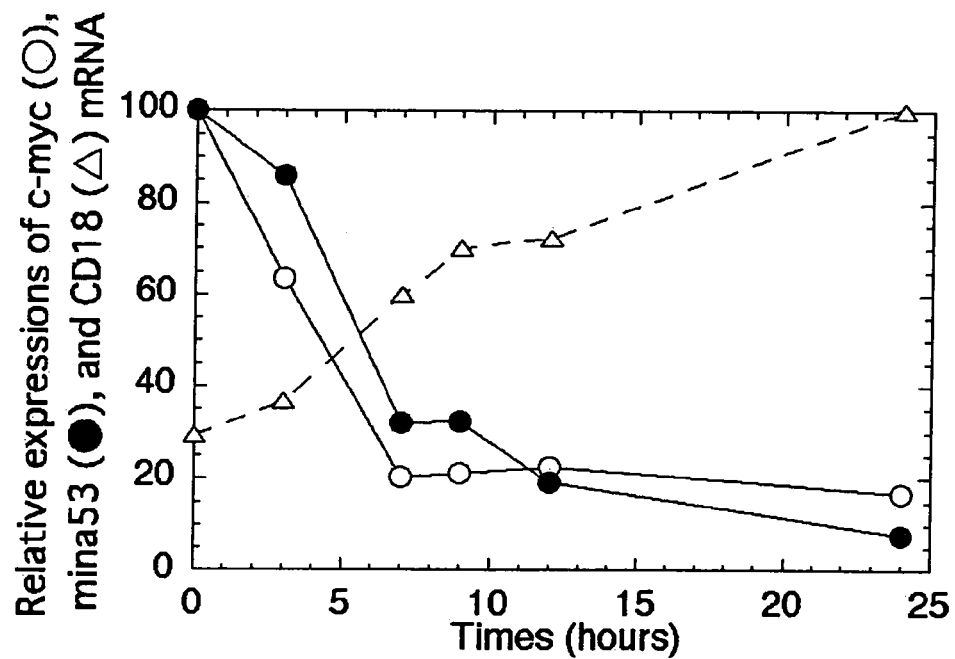
Figure 2:
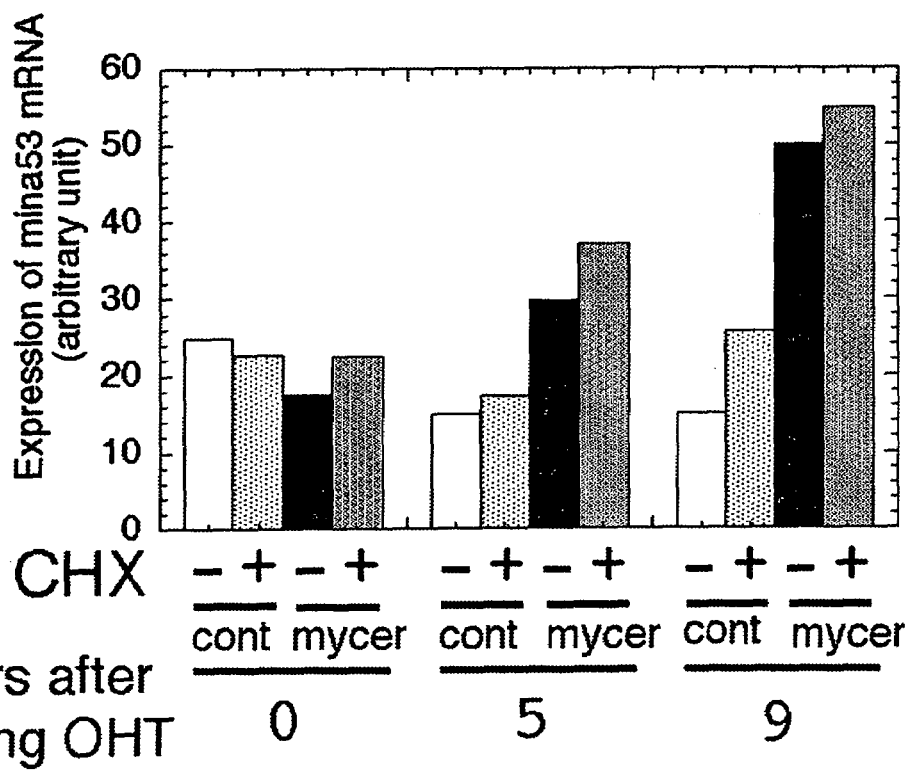

In the above-mentioned examples, the expression profile of mina53 mRNA which was examined by Northern blot analysis as shown in FIG. 2.

FIG. 2A shows the correlation of mina53 mRNA levels with c-myc expression levels in T98G cells. Serum-starved T98G cells were stimulated by the addition of serum to a final amount of 10%. RNA was isolated at the indicated time points and analyzed by Northern blotting to detect mina53 and c-myc mRNAs (left figure of FIG. 2A). 28 S and 18 S ribosomal RNAs are shown to indicate the amount of total RNA electrophoresed. The detected mRNAs were quantified and plotted (right figure of FIG. 2A). These results indicate the mina53 mRNA was expressed five-fold. This increase can be detected at 6 hours after the addition of serum and peaked at 12 hours. The amount of the expressed c-myc mRNA can be detected at 3 hours after the addition of serum and reached maximum at 12 hours. These results suggest that increasing c-myc mRNA expression induces increased mina53 mRNA expression.

FIG. 2B shows the parallel correlation of the decrease in mina53 mRNA levels and c-myc mRNA disappearance in human promyelocytic leukemia HL60 cells. This experimental system was used to investigate whether Myc-targeted genes are affected during the shut-off of Myc that accompanies hematopoietic differentiation. This experiment was conducted that RNA was isolated at the indicated time points by exposing human promyelocytic leukemia HL60 cells with 10 nM TPA, the same amount of RNA was analyzed by Northern blotting, and mina53, c-myc, and CD18 mRNAs were detected (left figure of FIG. 2B). Further, each mRNAs was quantified and plotted (right graph of FIG. 2B).

After 9 hours HL60 cells were cultured with 10 nM TPA, the expression of a differentiation marker CD18 started to increase and a 3-fold-induction was observed at 24 hours, confirming the differentiation in this system. At 3 hours after the addition of TPA, the level of c-myc mRNA started to decline and reached one fifth at 7 hours. Down-regulation of mina53 mRNA followed the decrease in c-myc mRNA, and the level of mina53 mRNA decreased to one fifth at 12 hours. These experiments demonstrate that the expression pattern of mina53 correlates with c-myc expression.

Next, the effect of c-Myc activation on mina53 mRNA was investigated. FIG. 2C shows the increase of mina53 mRNA levels in T98G cells expressing c-MycER protein (T98Gmycer-2 cells). After T98Gmycer-2 cells and parental T98G cells were cultured in the medium supplemented with 0.25% serum for 40 minutes 40 hours, cells were treated with 200 nM OHT, and RNA was isolated at the indicated time points. In the Figure, symbol + indicates that 20 µg/ml cycloheximide (CHX) was added 20 minutes before the addition of OHT. The same amount of RNA was analyzed by Northern blotting to detect mina53 mRNA (left figure of FIG. 2C). The detected mRNAs were quantified and plotted (right graph of FIG. 2C).

From the FIG. 2C, the mina53 mRNA level rose steadily for 9 hours in OHT-treated T98Gmycer-2 cells, showing nearly 3-fold induction. In contrast to this, the OHT treatment of T98G parent cells did not stimulate the mina53 mRNA level. Induction of mina53 mRNA by OHT in T98Gmycer-2 cells was maintained in the presence of the protein synthesis inhibitor cycloheximide. On the other hand, treatment with cycloheximide had little effect on the mina53 mRNA level in T98G parent cells. These results indicate that the mina53 gene is a direct target of Myc.

Figure 3:
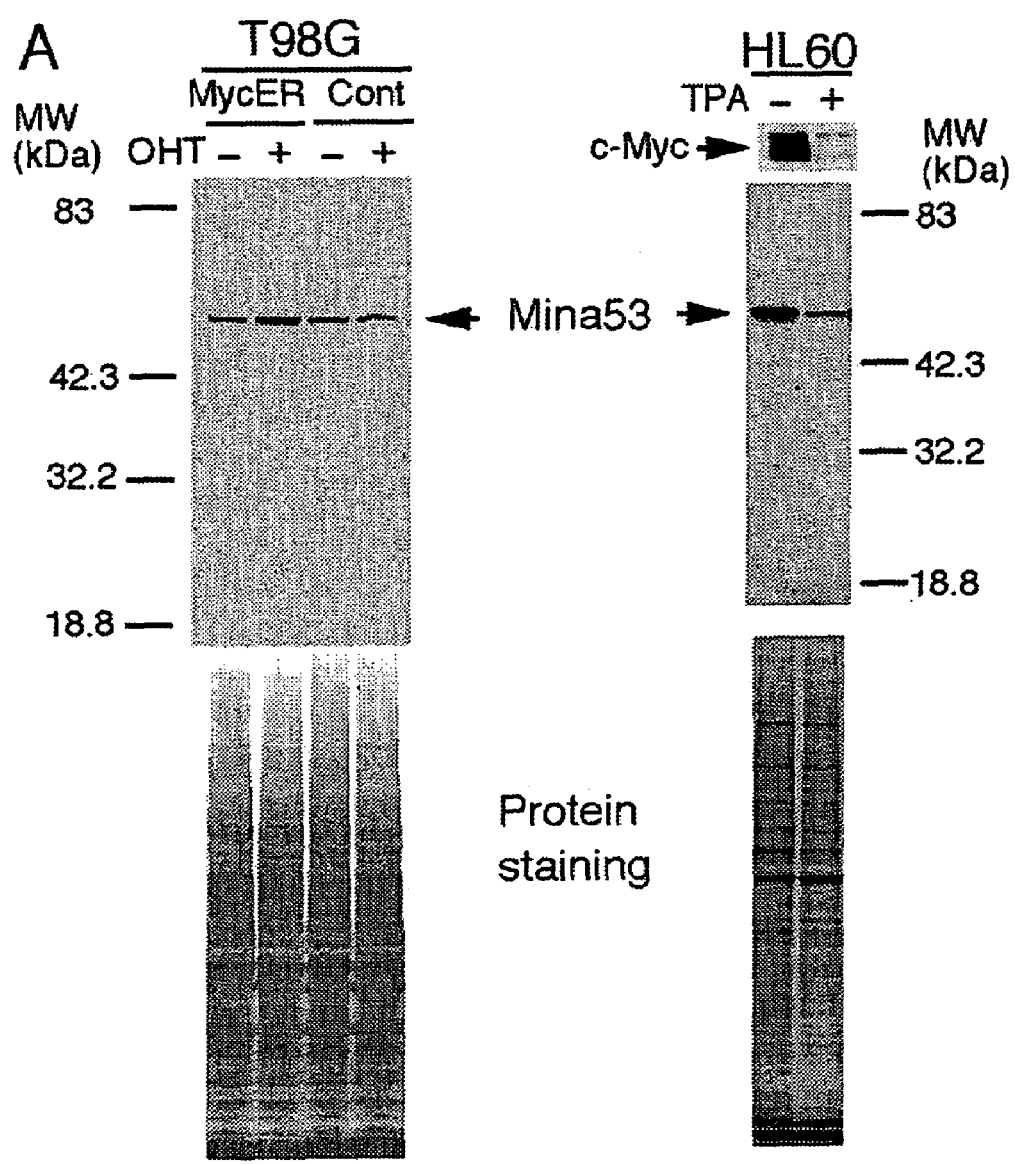
FIG. 3 shows the results of Western blot analysis of Mina53, left panel of FIG. 3A illustrates the elevated expression of Mina53 protein by Myc activation, right panel of FIG. 3A illustrates the decreased expression of c-Myc protein and Mina53 protein by decreasing the Myc expression with TPA.
Figure 3:
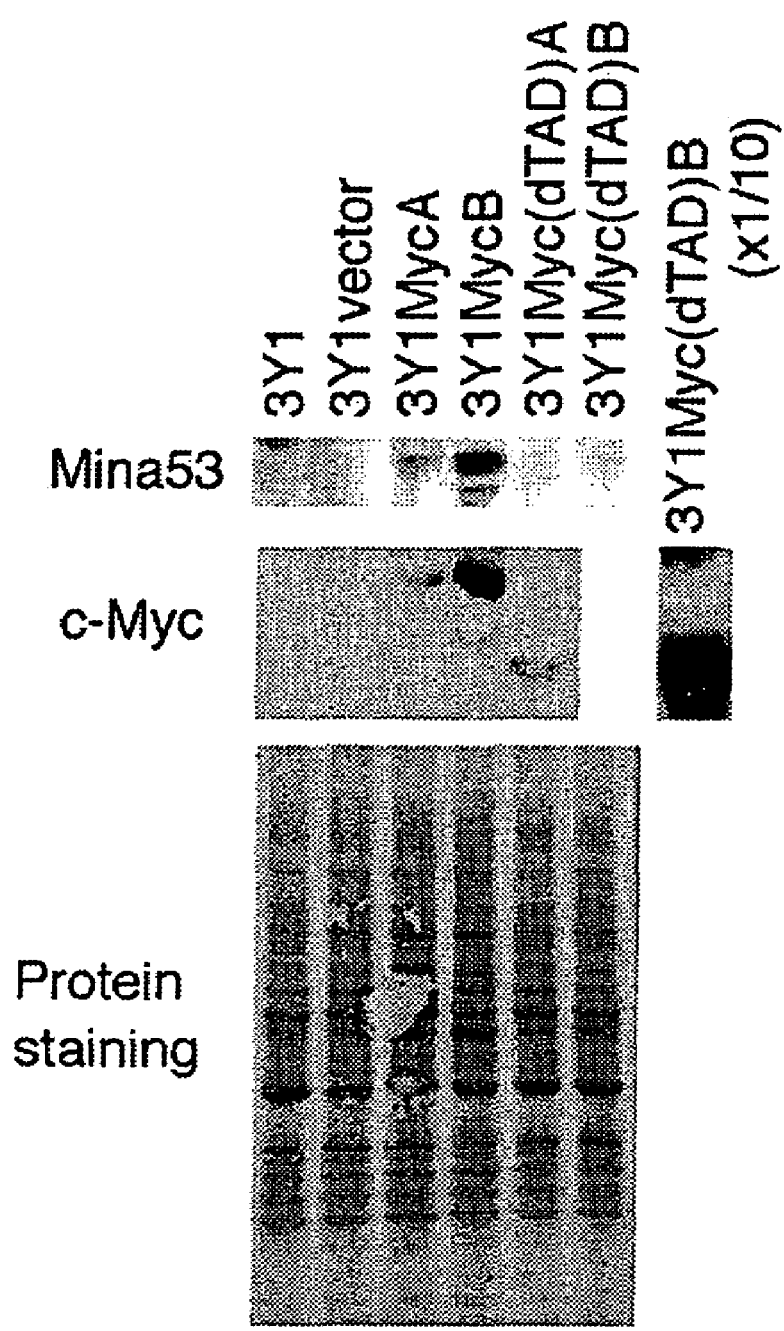

The elevated expression of Mina53 protein by Myc activation is explained by referring to FIG. 3. FIG. 3 is a Western blot analysis of Mina53 protein using a specific antibody. T98G and T98Gmycer-2 cells were cultured in the presence or absence of 200 nM OHT for 20 hours. Cell extracts were subjected to Western blotting using a specific antibody against human Mina53 protein (left panel). HL60 cells were cultured in the presence or absence of 10 nM TPA for 20 hours, and cell extracts were subjected to Western blotting using a specific antibody against human Mina53 protein and anti-c-Myc antibody (right panel). Profiles for protein staining are also shown (lower panel).

According to Western blotting with such specific antibody, the band having the same mobile degree as the predicted band based on amino acid sequence can be detected in T98G cells and HL60 cells (FIG. 3A). The band intensity of Mina53 was increased by activating c-Myc ER by OHT in T98Gmycer-2 cells. After HL60 cells were cultured in the presence of 10 nM TPA for 20 hours, the expressions of c-Myc and Mina53 protein were reduced.

As shown in FIG. 3B, expression vectors encoding human c-Myc, mutant c-Myc lacking the most part of the transcriptional activation domain (TAD), and an empty vector were stably introduced into rat 3Y1 fibroblast cells to establish cell lines. 3Y1MycA and 3Y1MycB cells carry and express the wild type human c-Myc, 3Y1Myc(dTAD)A and 3Y1Myc(dTAD)B cells carry and express mutant c-Myc deleted TAD, and 3Y1 vector carries an empty vector. Proteins were analyzed by Western blotting using anti-Mina53 antibody (upper panel), and anti-c-Myc antibody (middle panel). Profiles for conventional protein staining are also shown (lowest panel).

The control of Mina53 expression by c-Myc was also verified in rat fibroblast cell line 3Y1 (FIG. 3B). When human c-Myc was stably introduced in 3Y1 cells, the expression of Mina53 was increased in the dose-dependent manner (compare to the lanes for 3Y1, 3Y1 vector, 3Y1MycA and 3Y1MycB). In the mutant Myc which is a 3Y1 transfectant with c-Myc mutant lacking the transcriptional activation domain (TAD), expression of Mina 53 was not increased when Mina53 was expressed at a level comparable with that of wild type c-Myc (compare to the lanes for 3Y1MycA and 3Y1Myc(dTAD)A). Even at a much higher level than that of wild type c-Myc (compare to the lanes for 3Y1 vector, 3Y1MycB and 3Y1Myc(dTAD)B), expression of Mina53 protein was not increased. These results suggest that c-Myc activates the expression of mina53 using the transcriptional activation domain (TAD) of c-Myc.

FIG. 1A exhibits the genomic organization of human mina53. In the figure, boxes indicate exons; closed boxes mark the open reading flame (ORF), and the open boxes the 5' and 3' untranslated regions. Human mina53 gene consists of 12 exons, and exon 1a and exon 1b exist as two transcription sites. The direction of transcription is from left to right. The transcription starts from exon 1a or exon 1b. Exon 1b exists 0.25 kb downstream of exon 1a. The translation initiation site locates in exon 2. A stop codon (TAG) exists in exon 10. cDNA encoding 464 amino acids (lacking 297Q) lacks the first 3 bp of exon 7. Exon 5' between exon 5 and exon 6 encodes the 101-bp sequence, which is inserted in the center of the main cDNA.

Human genomic DNA sequences, which include mina53 cDNA sequences, were found in the HTGS (GenBankAcc: AC026100, AC073245, and AC024892). Since the length of intron 2 (between exon 2 and exon 3) was different from the GenBank data, oligonucleotides corresponding to the sequences in exon 2 and exon 3 using as primers were amplified by PCR, and its length was determined to be 5.2 kb. The mapping data from UCSGenomeBrowser showed that mina53 gene maps to the third chromosome (3q12.1).

FIG. 1B shows that exon 1b has two E-boxes (CACGTG element). The first and second boxes of these two E-boxes were named as E-box 1 and E-box 2, respectively.

In order to examine the promoter activity for mina53 gene, reporter plasmid, pMina(W)luci was constructed by ligating a human mina53 genomic DNA fragment containing the upstream region from exon 1a, exon 1a, exon 1b and part of intron 1) to firefly luciferase cDNA (FIG. 1B). In the figure, pMina(dE)luci means reporter plasmid lacking the part having two E-box, pMina(mE1/2)luci means reporter plasmid mutated in two E-boxes, pMina(mE1)luci means reporter plasmid mutated in E-box 1, and pMina(mE2)luci means reporter plasmid mutated in E-box 2.

FIG. 1C shows DNA fragment has promoter activity according to the transient expression assay in T98 cells.

The activation of c-MycER by OHT achieved three-fold increased luciferase activity. This stimulation is matched to that observed against mina53 mRNA (FIG. 2C).

When two E-boxes of pMina(W)luci were deleted from pMina53(W)luci, the luciferase activity was not increased even by the activation of the c-MycER chimeric protein (FIG. 2C, data of pMina53(W)luci). The expression from pMina53(mE2/E2)luci, in which two E-boxes (CACGTG elements) were mutated to CACCTG was not increased by the activation of c-Myc. These results illustrate that the expression of pMina53(W)luci was activated through E-box stimulated by CACGTG element.

In order to determine whether CACGTG element of E-boxes is functional, reporter plasmid pMina(mE1)luci and pMina53(mE2)luci having CACCTG element in place of CACGTG of the sequences of each E-boxes, thus having different CACGTG element were constructed respectively (FIG. 1B). As shown in FIG. 1C, mutation of E-box 1 had little effect. On the other hand, mutation of E-box 2 severely decreased the stimulation by c-Myc. These results suggest that c-Myc functions through E-box 2.

To examine c-Myc protein binding to the endogenous mina53 gene in vivo during proliferation of HL60 cells, chromatin immunoprecipitation (ChIP) was performed (Boyd, K. E., et al.: (1997) Mol. Cell. Biol. 17, 2529-2537; Boyd, K. E., et al.: (1998) Proc. Natl. Acad. Sci. USA 95, 13887-13892). After immunoprecipitation with anti c-Myc antibody, the endogenous mina53 gene fragment in each sample was monitored by PCR that specifically amplify part of exon 1b and intron 1 in the mina53 gene.

Figure 4:
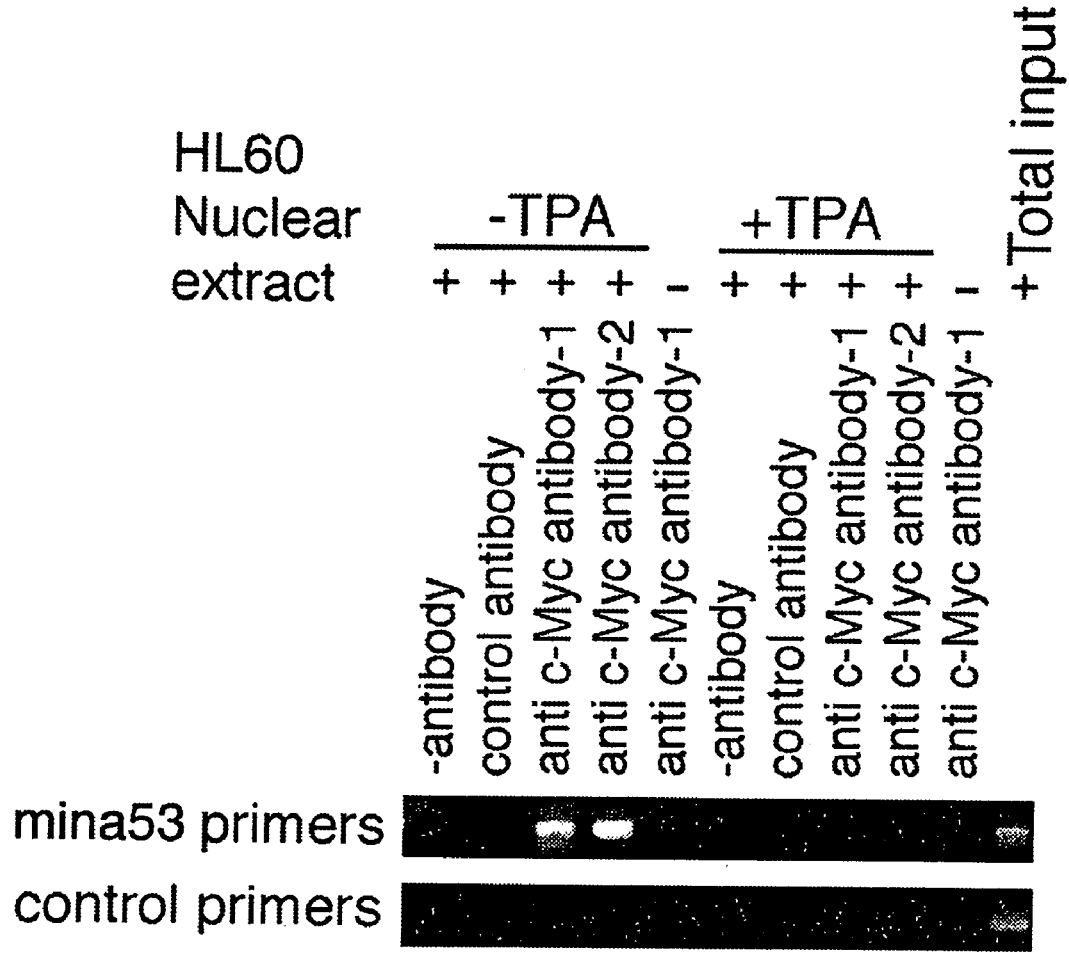
FIG. 4 shows the results of chromatin immunoprecipitation experiments using HL60 cells.

As shown in FIG. 4, two different anti-c-Myc antibodies immunoprecipitated the mina53 DNA from HL60 cells in the proliferating phase, whereas mina53 gene fragment was not immunoprecipitated by the co-cultivation with TPA. The detection and purification of mina53 genomic DNA fragment proves that the mina53 genomic DNA fragment is dependent on c-Myc binding to the mina53 gene, because nonspecific antibody did not immunoprecipitate mina53 DNA fragments. Additionally, binding of c-Myc detected in the mina53 gene is specific, since antibodies against c-Myc did not immunoprecipitate the genomic DNA fragment containing an E-box that is located in a chromosomal region without any detectable gene in chromosome 22. These results demonstrate that the mina53 gene is bound to c-Myc specifically at the proliferating phase of HL60 cells.

Figure 5:
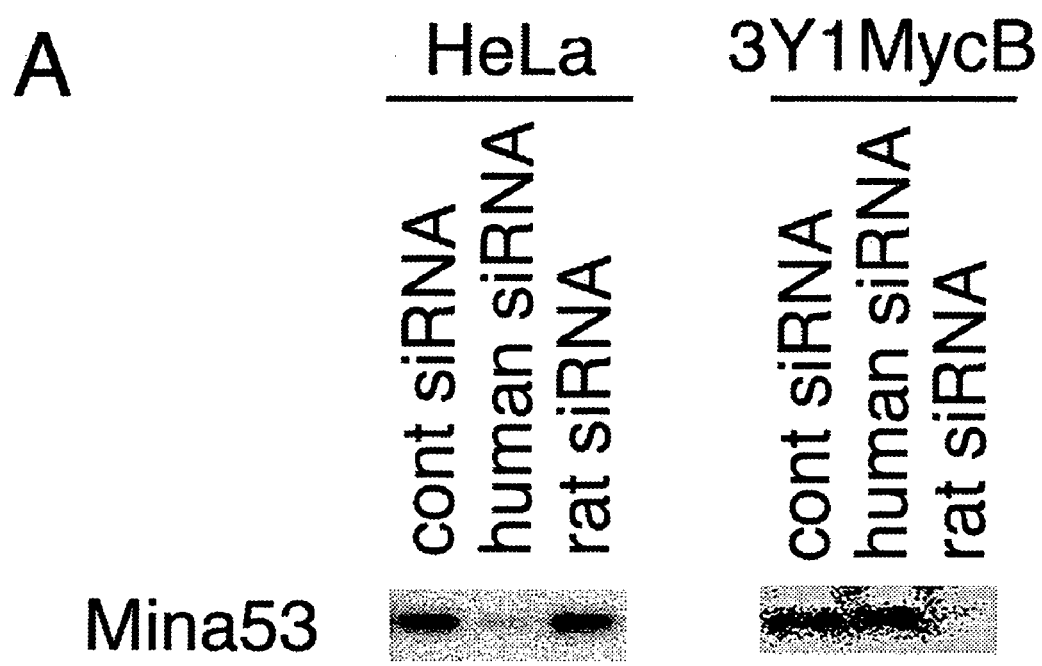
FIG. 5 shows the reduction of Mina53 protein expression by RNA interference and its effect on cell proliferation.
Figure 5:
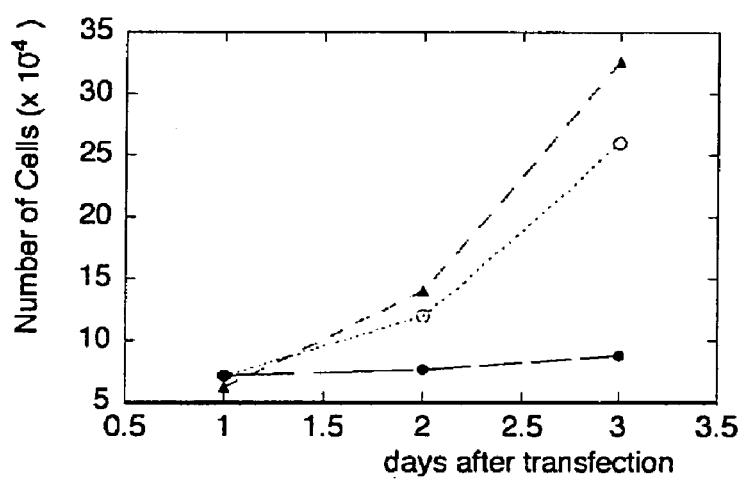
Figure 5:
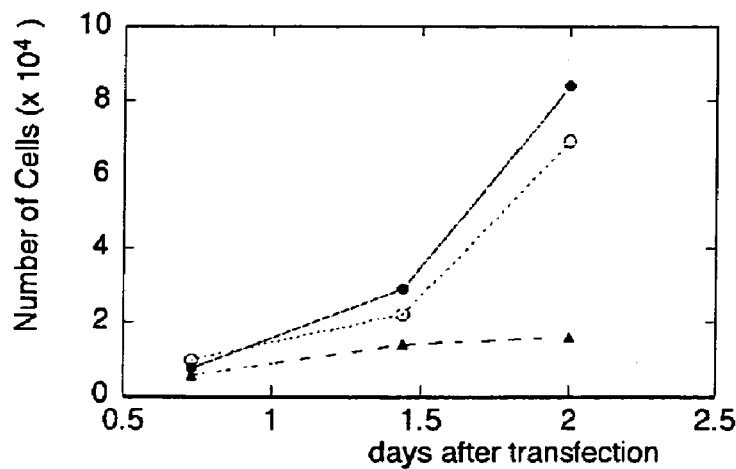

Referring to FIG. 5, the followings illustrate that Mina53 is involved in proliferation of HeLa Cells and 3Y1 Cells highly expressing c-Myc.

To investigate the biological function of mina53, as mentioned above, the expression of Mina53 protein was specifically inhibited by using siRNA duplex and monitored Mina53 protein 40 hours after siRNA transfection.

As shown in FIG. 5A, the expression of Mina53 protein was specifically reduced by the cognate siRNA duplex in HeLa cells but by neither an siRNA duplex with inverted mina53 sequence (a control) nor a duplex directed against rat mina53. The expression of Mina53 protein was specifically reduced by the cognate siRNA duplex in rat 3Y1 cells highly expressing c-Myc (3Y1MycB) but by neither the control siRNA nor the duplex directed against human mina53.

As shown in FIG. 5B, when Mina53 expression was reduced, cell proliferation was severely suppressed, i.e. proliferation of HeLa and 3Y1MycB cells were almost completely stopped by transfection of siRNA duplex directed against human and rat mina53, respectively.

Further, the anti-Mina53 monoclonal antibody of the present invention can be shown to recognize the single band with the molecular weight of 53 kDa according to Western blot analysis using leukemia cell lines HL60 when the expression of the protein Mina53 was investigated by Western blot analysis (FIG. 6A, lane 1). The signal of band with 53 kDa was reduced by treating with TPA according to the immunoblotting analysis using the above-mentioned anti-Mina53 monoclonal antibody (FIG. 6A, lane 2). On the contrary, the expression of β-actin was not specifically reduced even by treatment with TPA (FIG. 6A, lanes 1 and 2).

In another experiment using protein which was cell-fused with green fluorescent protein (GFP) expressed in the HeLa cells the anti-Mina53 monoclonal antibody generated the single band of protein Mina53 which was cell-fused with green fluorescent protein (GFP) expressed in HeLa cells in addition to the endogenous protein Mina53.

The expression of human Mina53 protein was examined in three kinds of the colon tumor cell lines, HT-29, WiDr and SW620 in the proliferation phase according to immunoblotting analysis with anti-Mina53 monoclonal antibody of the invention. As a result, the anti-Mina53 monoclonal antibody recognized a single band of 53 kDa in the three cell lines (FIG. 6A, lanes 3 to 5). The results indicate that these cell lines express Mina53 and that the anti-Mina53 monoclonal antibody specifically recognizes Mina53 protein in colon tumor cell lines without cross-reactivity with other proteins.

The expression level of Mina53 in these cell lines is much higher than that of Mina53 in HL60 cells experimentally reduced by TPA (FIG. 6A, lanes 2 to 5). On the other hand, the levels of actin in the three colon tumor cell lines were not higher than that of HL60 cells treated with TPA. These results suggest that the three colon tumor cell lines contain a higher level of Mina53 protein than terminally differentiated HL60 cells.

The investigation of the localization of Mina53 in colon tumor cells according to the double immunofluorescence staining of cells using anti-Mina53 monoclonal antibody and anti-nucleolin rabbit antibody illustrates that the anti-Mina53 monoclonal antibody stained specifically nuclei in SW620 cells with strong dotted staining in nucleoli that overlapped with the signals for nucleolin. The other two cell lines also showed a similar pattern of immunofluorescence staining. These results indicate that protein Mina53 locates in the nucleus with condensed states in nucleolus in the colon tumor cell lines, as we previously demonstrated in HeLa cells (Tsuneoka, M., et al., ibid).

(Expression of Protein Mina53 in Colon Tumor Tissues)

Figure 7:
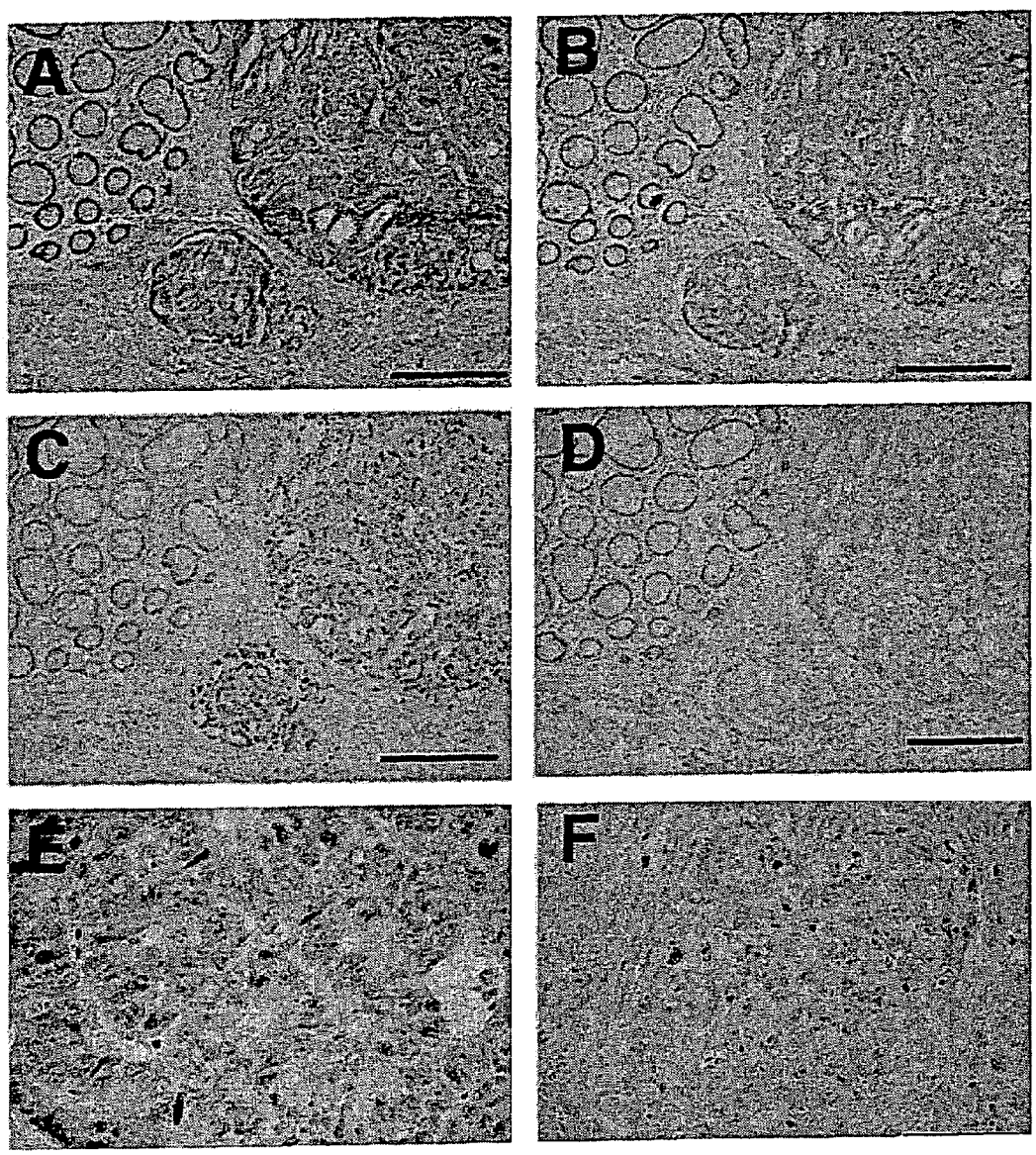
FIG. 7 shows the results of immunohistochemical staining of Mina53 and Ki-67 proteins in colon cancer tissues.
Figure 8:
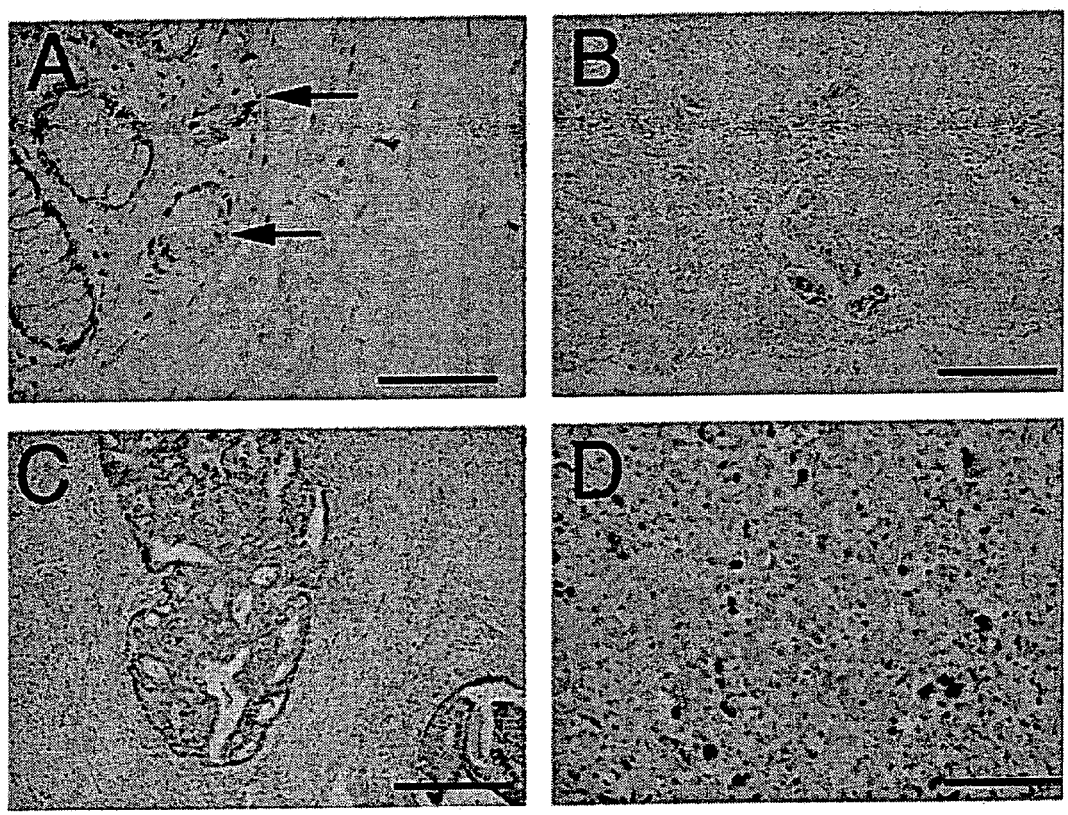
FIG. 8 shows the immunohistochemical staining of Mina53 in tumors with invasive and metastatic potential.

The anti-Mina 53 monoclonal antibody of the present invention was used to detect Mina53 protein in colon tumor tissues and HE staining was used to demarcate the tumor areas. The section shown in FIG. 7A contained moderately differentiated colon tumor cells. FIG. 7B showed marked staining for Mina53 in tumor areas, while most non-neoplastic epithelial cells around the tumors showed little staining. Staining is found mainly in nuclei (FIGS. 7, E and F) with dotted staining (probably nucleoli) showing a pattern similar to those obtained from the colon tumor cell line (FIG. 7B). No nuclear staining was observed when the section was incubated without said antibody (FIG. 7D) or when the section was incubated in the presence of an excess amount of recombinant Mina53 protein. In some sections of tumor tissues, tumor cells were found in lymphatic vessels just beneath the epithelium located away from the main neoplastic area. The anti-Mina53 monoclonal antibody of the present invention markedly stained these tumor cells, while the surrounding non-neoplastic cells were only weakly stained (FIG. 8A). In addition, tumor cells that had penetrated into lymphatic vessels in deeper layers of the colon also showed strong immunoreactivity to Mina53 protein, while surrounding non-neoplastic cells were not stained (FIG. 8B). Further, the anti-Mina53 monoclonal antibody also stained deeply invading tumors (FIG. 8C) and distinguished poorly differentiated tumor cells in fibrous stroma (FIG. 8D), while non-neoplastic cells surrounding these tumor cells were not stained. These results suggest that Mina53 protein is highly expressed in tumors with invasive and metastatic potential.

(Mina53 Expression by Pathological Grade of Colon Cancer)

Mina53 was detected in specimens from patients with colon adenocarcinoma and adenoma, using the immunohistochemical staining method. A summary of the immunohistochemical staining is presented in Table 1. As shown in Table 1, protein Mina53 was expressed in all pathological grades of colon cancer. Namely, well (FIG. 9A), moderately (FIG. 7B), and poorly (FIG. 2F) differentiated tumors were all markedly stained for Mina53 with average staining indexes of 2.28, 1.78, and 1.85, respectively (Table 1). These results suggest that there is no obvious correlation between the pathological grade of tumor and staining intensity, although there was a slight tendency for well differentiated tumor to show higher staining intensity than poorly and moderately differentiated ones. In addition, Mina53 protein was highly expressed in the adenoma (FIG. 9C), suggesting that the elevated expression of Mina53 protein is a general and relatively early event in colon carcinogenesis. As described above, staining was confined to the nucleus in all cases (FIGS. 7E and 7F).

In conclusion, the study of the expression of Mina53 protein in colon tumor cell lines and colon tumor tissues was performed by using the anti-Mina53 monoclonal antibody. The examined three colon tumor cell lines showed prominent expression of protein Mina53. The results of this study showed that almost all colon tumor tissues examined exhibited elevated expression of Mina53. Mina53 protein was expressed in colon cancer of all pathological grades, well, moderately, and poorly differentiated, while most non-neoplastic cells showed little or no staining for Mina53 protein. The elevated expression of Mina53 in tumor cells was observed irrespective of the location of the tumor cells; that is, tumor cells in primary neoplasia, invading tumors and tumors in lymphatic vessels as well as isolated tumor cells were prominently stained for Mina53 protein.

TABLE 1

| Patient | Grade | % Stained Cancer Cells | | Staining Intensity | | Staining Index | |
|---|---|---|---|---|---|---|---|
| | | Mina53 | Ki-67 | Mina53 | Ki-67 | Mina53 | Ki-67 |
| 1 | Poor | 84.5 | 46.2 | 1 | 1 | 0.85 | 0.46 |
| 2 | Poor | 86.3 | 63.2 | 3 | 3 | 2.91 | 2.44 |
| 3 | Poor | 79.6 | 88.9 | 2 | 3 | 1.59 | 2.67 |
| | * | 100.0 | 96.3 | 2 | 2 | 2.00 | 1.93 |
| | ** | 0 | 31.9 | 0 | 2 | 0.00 | 0.64 |
| 4 | Poor | 94.2 | 52.4 | 2 | 3 | 1.89 | 1.57 |
| 5 | Poor | 100.0 | 100 | 2 | 3 | 2.00 | 3.00 |
| 6 | Moderate | 94.3 | 81.6 | 2 | 2 | 1.89 | 1.63 |
| 7 | Moderate | 100.0 | 76.2 | 3 | 3 | 3.00 | 2.29 |
| 8 | Moderate | 97.5 | 87.4 | 2 | 3 | 1.95 | 2.62 |
| 9 | Moderate | 100.0 | 83.6 | 1 | 3 | 1.00 | 2.50 |
| 10 | Moderate | 92.4 | 75.0 | 2 | 2 | 1.85 | 1.50 |
| 11 | Moderate | 79.2 | 62.1 | 2 | 2 | 1.58 | 1.24 |
| 12 | Moderate | 89.0 | 54.2 | 1 | 2 | 0.89 | 1.08 |
| 13 | Moderate | 100.0 | 60.1 | 1 | 3 | 1.00 | 1.80 |
| 14 | Moderate | 95.5 | 84.8 | 3 | 3 | 2.87 | 2.54 |
| 15 | Well | 80.1 | 72.9 | 2 | 2 | 1.60 | 1.46 |
| 16 | Well | 100.0 | 63.5 | 2 | 2 | 2.00 | 1.27 |
| 17 | Well | 93.8 | 50.0 | 3 | 2 | 2.81 | 1.00 |
| 18 | Well | 100.0 | 100.0 | 3 | 3 | 3.00 | 3.00 |
| 19 | Well | 92.7 | 84.6 | 2 | 3 | 1.85 | 2.54 |
| 20 | Well | 78.7 | 74.0 | 2 | 3 | 1.57 | 2.22 |
| 21 | Well | 98.9 | 57.0 | 2 | 3 | 1.98 | 1.71 |
| 22 | Well | 92.7 | 43.1 | 3 | 3 | 2.78 | 1.29 |
| 23 | Well | 98.3 | 80.0 | 3 | 3 | 2.95 | 2.40 |
| 24 | Adenoma | 90.0 | 42.6 | 3 | 2 | 3.00 | 0.85 |

* The area contained mucinous adenocarcinoma cells.
** The cancer had a morphology similar to acinar cell carcinoma of the pancreas.

(Comparison of Staining Patterns Between Mina53 and Ki-67 in Colon Tumor Tissues)

Serial sections were also stained with anti-Ki-67 monoclonal antibody (MIB1) to compare the staining pattern with that of anti-Mina53 monoclonal antibody. As reported before (Cattoretti, G., et al.: J. Pathol., 1992, 168: 357-563; Jansson, A., Sun, X. F.: APMIS 1997, 105: 730-734; Saarnio, J., et al.: Am. J. Phathol, 1998, 153: 279-285), anti-Ki-67 monoclonal antibody stained colon tumor tissues intensely like anti-Mina53 monoclonal antibody (FIGS. 7C and 9B). In most cases both antibodies against Ki-67 and Mina53 stained tumor cells similarly, as shown in FIGS. 7B,8C, 9A and 9B, and Table 1.

When the percentages of tumor cells in a microscopic field stained for both Ki-67 and Mina53 were compared, differences were found between the two antibodies. In the majority of the cases, the percentage of Mina53-expressing cells was higher than that of Ki-67 (FIGS. 9A and 9B). In a few cases, the percentage of Mina53-expressing cells was similar to that of Ki-67 (Table 1).

In one case (patient number 3), the staining pattern was rather complex because of the examined sections contained three different types of cancer. Two areas with poorly differentiated adenocarcinoma cells and mucinous adenocarcinoma cells showed similarly high percentages of positive cells for both Mina53 protein and Ki-67 (Table 1). In the third area, however, the tumor had morphologically similar to acinar cell carcinoma of the pancreas and was very weakly stained by anti-Mina53 monoclonal antibody but was strongly stained by anti-Ki-67 monoclonal antibody, although the percentage of positive cells was low as compared to the former two areas (Table 1). In the case of the adenoma, almost all cells in the neoplastic areas were intensely stained by anti-Mina53 antibody, while fewer cells were stained by anti-Ki-67 antibody (FIGS. 9C and D). Although there was a fewer exception, the results suggest that the percentage of Mina53-expressing cells was characteristically higher than that of Ki-67-expressing cells.

(Comparison Between Staining Patterns of Mina53 and Ki-67 in Non-Neoplastic Colon Tissues)

Figure 9:
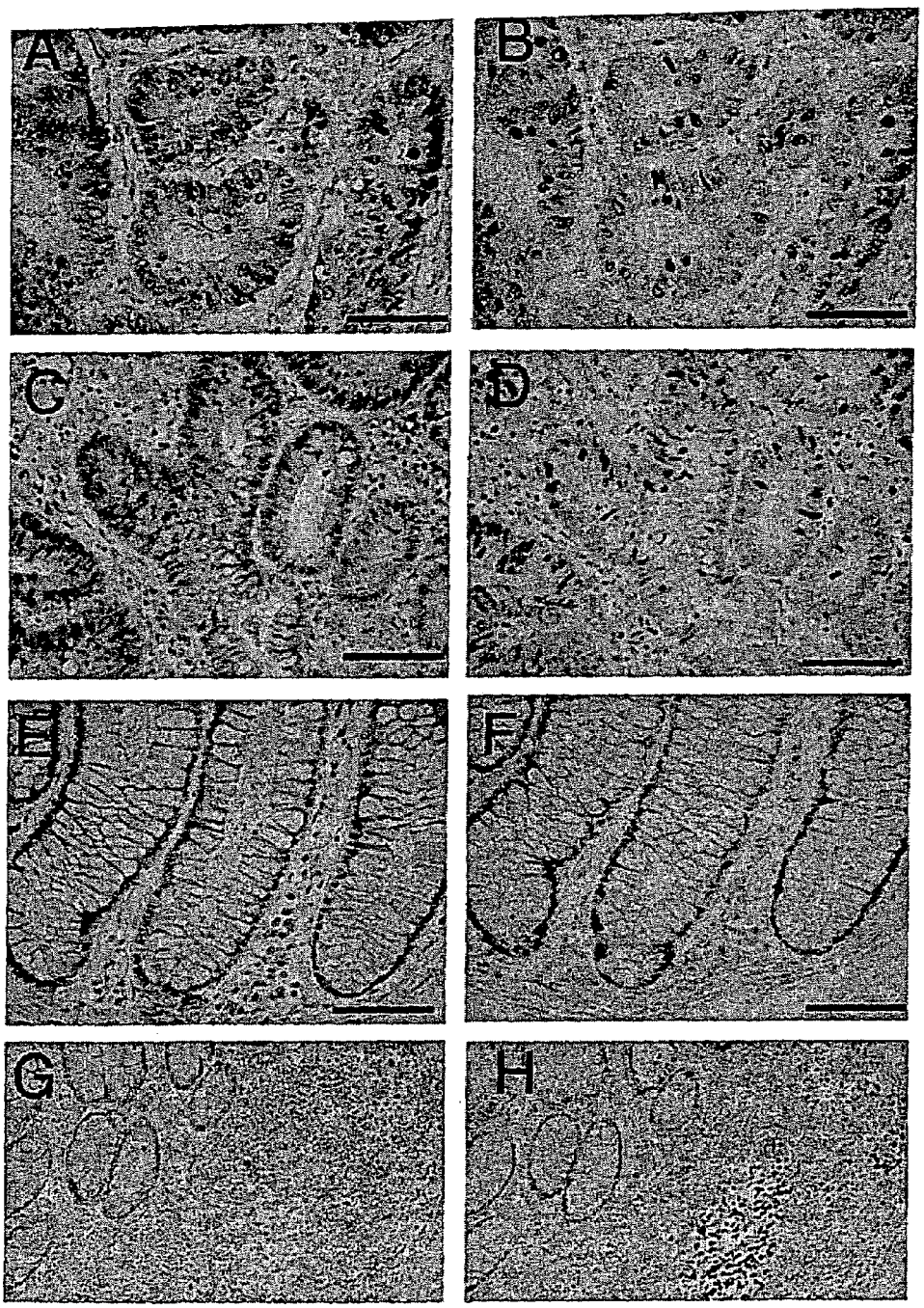
FIG. 9 shows the comparison of staining patterns between anti-Mina53 monoclonal antibody (left column) and anti-Ki-67 monoclonal antibody (right column) in serial sections of cancerous, adenomatous, and non-neoplastic colon epithelium.

In some areas of non-neoplastic colon tissues, antibody against Ki-67 stained cells intensely, whereas the antibody against Mina53 stained those cells only weakly. The staining by anti-Ki-67 monoclonal antibody was observed in nuclei of cells in the lower third of the crypts, the zone of active cell proliferation (FIG. 9F). The staining intensity in non-neoplastic colon tissue crypts did not differ significantly from cells found in the tumor areas (FIGS. 9, B and F). On the other hand, anti-Mina53 monoclonal antibody only faintly stained nuclei of these cells, and the intensity was far weaker than cells found in the tumor areas (FIGS. 9, A and E). Further, a lymphoid germinal center, which contains cells with high mitotic activity, was intensely stained by Ki-67 antibody, but was rarely stained by ant-Mina53 monoclonal antibody (FIGS. 9, G and F).

These results confirm that tumor cells express Mina53 protein at a higher ratio than Ki-67 which is widely used as cell-proliferating maker. Antibody to Ki-67 strongly stained tumor cells as well as some well-proliferating normal cells, including cells in the lower crypts and lymphoid germinal centers. On the other hand, antibody to Mina53 rarely stained cells in non-neoplastic areas.

These results indicate that high expression of Mina53 can be regarded as a characteristic feature of colon cancer. Thus, the expression of Mina53 can be used as a marker for colon cancer and may be helpful in finding tumor cells that have invaded normal tissues. In addition, Mina53 staining may also serve as an additional prognostic marker.

Somatic mutations in the APC gene were found in more than 60% of colon cancers (Miyoshi, Y. et al.: Hum. Mol. Genet., 1992, 1: 229-233; Powell, S. M., et al.: Nature 1992, 359: 235-237). Mutations of β-catenin were also found in some colon tumors lacking APC mutations (Morin, P. J., et al.: Science 1997, 275: 1787-1790; Sparks, A. B., et al.: Cancer Res., 1998, 58: 1130-1134). The main function of APC protein is thought to be the regulation of free β-catenin in concert with glycogen synthase kinase 3β (GSK-3β) and axin proteins (Hinoi, T., et al.: J. Biol. Chem., 2000, 275: 34399-34406). Loss of APC function, inactivation of axin (Behrens, J., et al.: Science 1998, 280: 596-599) or activating β-catenin mutations (Polakis, P.: Curr. Opin. Genet. Dev., 1999, 9: 15-21) results in cellular accumulation of β-catenin, which, when translocated to the nucleus, serves as an activator of T-cell factor (Tcf)-dependent transcription leading to increased expression of several specific target genes (Roose, J., Clevers, H.: Biochem. Biophys. Acta 1999, 1424: M23-M37). Recently, it was shown that c-myc was identified as a target of APC pathway, and evoked by the loss of the function of APC gene or overexpression of β-catenin (He, T. C., et al.: ibid). Therefore, inactivating mutations of APC or axin or activating mutations of β-catenin would result in overexpression of c-myc. As a result, it is considered that expression of Mina53 increases. It appears therefore that mina53 is a downstream, indirect target of the APC/β-catenin pathway that is implicated in colon carcinogenesis.

These results show that the high expression of Mina53 is regarded as the typical characteristics of colon tumors. Therefore, the expression of Mina53 is used as a marker for the colon tumors and is useful for finding tumor cells invaded into normal cells. In addition, the staining of Mina53 is also useful as prognostic marker.

The expression pattern of Mina53 was compared with that of Ki-67, a widely used biomarker for cell proliferation. The percentage of Mina53-expressing cells was characteristically higher than that of Ki-67-expressing cells in most tumor tissues (Table 1). This may be due to the fact that mina53 is a Myc-target gene. c-myc is expressed continuously in all phases of the cell cycle in proliferating cells (Rabbits, P. H., et al.: EMBO J 1985, 4: 2009-2015; Waitz, W., Loidl, P.: Oncogene 1991, 6:29-35). On the other hand, Ki-67 is preferentially expressed in proliferating cells in late G1, S, M and G2 phases (Gerdes, J., et al.: Int J Cancer 1983, 31: 13-20; Gerdes, J., et al.: J Immunol. 1984, 133: 1710-1715). Because Mina53 is induced by c-myc, it is reasonable that Mina53 is more widely expressed than Ki-67 in tumor tissues.

Cells in the crypts, which have been shown to grow well, were intensely stained by the antibody against Ki-67, but only weakly by the antibody against Mina53. Lymphoid germinal centers that contain non-neoplastic but proliferating cells were weakly stained by anti-Mina53 antibody but strongly stained by anti-Ki-67 antibody. The present inventors show that Mina53 is an important factor for cell proliferation in two kinds of cultured cell lines of which highly express c-myc, namely, human cervical carcinoma HeLa cells and rat fibroblast cell (Tsuneoka, M., et al.: ibid). Thus, it is possible that Mina53 may play a role in cell proliferation only in some restricted types of cells. Alternatively, normal cells in the crypts and lymphoid germinal centers may require smaller amounts of Mina53 for cell proliferation or these cells may express a protein with a similar function as Mina53 protein. Either way, since tumor cells were intensely stained by anti-Mina53 antibody as compared to non-neoplastic cells in vivo, Mina53 may have some functions in carcinogenesis.

Staining index obtained by staining esophageal cancer tissues by anti-Mina53 monoclonal antibody was compared with staining index obtained by staining by anti-Ki-67 monoclonal antibody that is currently used for staining human esophageal cancer to observe the correlation of the staining degree but to recognize the clear difference. Namely, as shown in FIG. 13, high staining degree by anti-Ki-67 monoclonal antibody exhibits that the staining degree by anti-Mina53 monoclonal antibody also became high. On the other hand, there were observed some high staining degree by anti-Mina53 monoclonal antibody among cases without almost any staining degree by anti-Ki-67. This shows that anti-Mina53 monoclonal antibody stains the esophageal tissues better than anti-Ki-67 monoclonal antibody.

Then, the correlation between the survival months after operation of esophageal cancer, and Mina53 staining index and Ki-67 staining index was examined in 33 cases of which survival months were confirmed. As shown in FIG. 12, clear correlation can be observed between the survival month and Mina53 staining index ($p<0.001$). On the other hand, such correlation was not observed in Ki-67.

Then, the patients suffered from esophageal cancer were divided into two classes with low or high Mina53 expression, and analyzed according to Kaplan-Meier method. As shown in FIG. 12(A), clear differences in the accumulated survival rates of two groups were found. While the same analysis to Ki-67 was carried out, clear difference was not observed unlike Mina53 as shown in FIG. 12(B). Then, the relationship between the survival month after the operation of patients suffering from esophageal cancer, and Mina53 staining index and Ki-67 staining index is summarized in Table 2.

TABLE 2

|  | Case Numbers | Correlation | p value |
| --- | --- | --- | --- |
| Mina53 | 33 | −0.436 | 0.0104 |
| Ki-67 | 33 | −0.83 | 0.6499 |

The above results suggest that the staining degree by anti-Mina53 monoclonal antibody is correlated with the malignant degree.

There is the part called JmjC domain in the region of the amino acid sequence 128-271 of Mina53 (Tsuneoka, M. et al.: ibid). This domain was recently identified on the basis of the sequence similarity among many genes, and the proteins having JmjC domains almost all possess DNA-binding or chromatin-binding domains (Clissold, P. M., Ponting, C. P.: Trends Biochem Sci 2001, 26: 7-9). The JmjC domains are expected to adopt the cupin fold and candidates for metalloenzymes that regulate the re-modeling of chromatin (Clissold, P. M., Ponting, C. P.: ibid). The independent process based on the changes not associated with a series of genetic changes and changes of the gene sequence all of which progress cancer results in cancer (Fearnhead, N. S., et al.: Br Med Bull 2002, 64: 27-43). Chromatin remodeling, one of the changes not associated with the changes of gene sequence affects the expression of gene and becomes a cause of carcinogenesis. The localization of Mina53 in nucleus is considered to support the possibility that Mina53 is related to the progress of tumor by the remodeling of chromatin. However, in order to make clear this hypothesis, it is necessary to determine whether the remodeling of chromatin is a true function of Mina53 or not.

Since it is clear that the activation of cancer genes is associated with carcinogenesis, pharmacological strategies for the treatment of human cancers for the inactivation of such cancer genes as the goal becomes important. Based on such strategies, it is expected that medicaments will be designed to inactivate cancer genes and that many more cancer treatments are developed. However, it is considered that the use of such medicaments for a long period of time mortally cleaves the signal pathway to the normal cells and severe toxicity is caused (Jain, M, et al.: Science 2002, 297: 102-104). Further, a recent study has made clear that myc family cancer genes are central regulators of cell growth and such genes are decisively necessary in the normal biological processes inclusive of organ development and regeneration (Henriksson, M, Luscher, B.: Adv Cancer Res 1996: 109-182; Grandori, C, et al.: Annu Rev Cell Dev Biol 2000, 16: 653-699; Luscher, B.: Gene 2001, 277: 1-14; Stanton, B. R., et al.: Genes Dev 1992, 6: 2235-2247; Sawai, S, et al.: Development 1993, 117: 1445-1455). As mentioned above, c-myc regulates the expression of various genes and the specific Myc target gene is believed to play a substantive role in each function of Myc.

INDUSTRIAL APPLICABILITY

The novel cancer-associated mina53 gene which is regulated by c-myc and identified by the present invention can be applied variously in the cancer-associated field since its expression is regulated directly by cancer myc gene, it encodes Mina53 protein having 53,000 of molecular weight in nucleus, it is associated with cell proliferation, and its expression was specifically increased in cancer tissues. Namely, the novel mina53 gene of the present invention is applicable to cancer diagnosis because its expression increases specifically in cancer cells. Since the suppression of proliferation of cancer cells is observed to inhibit the expression of Mina53 protein, it is applicable to develop novel medicaments for inhibiting the expression of mina53 gene, or inhibiting specifically Mina53 activity by gene therapy and the like.

The mina53 gene and its products of the present invention can diagnose abnormal cells such as cancer cells and control the proliferation of such cells.

Further, the anti-Mina53 monoclonal antibody of the present invention can be used to confirm the high expression of Mina53 protein in human colon cancer cells, and Mina53 protein is highly expressed in the primary cancer tissues or invading cancer cells in muscle coat or lymph vessel in human colon tissues compared with the normal epithelium. The expression of Mina53 protein is likely to the expression of Ki-67 which is widely used as a cell proliferating marker. But, it is confirmed that the ratio of the positive cells against the expression of Mina53 protein in cancer cells is higher than that of Ki-67 protein. Further, in the active region of cell division of normal colon epithelium, strong expression of Ki-67 was observed, but the expression of Mina53 was not high. Moreover, strong expression of Ki-67 in the germinal center of lymphatic follicle was observed, but the expression of Mina53 was not high. This suggests that Mina53 protein possesses higher specificity to cancer than Ki-67.

The expression of Mina53 can be used as markers for colon cancers since these results demonstrate that the expression of Mina53 is an early event of colon cancer and is deemed to be a typical characteristic of colon cancer. Mina53 also can be used to detect invading cancer cells in normal tissues. Further, the staining of Mina53 is useful as a prognostic marker.

The anti-Mina53 monoclonal antibody was confirmed to be able to stain esophageal cancer cells better than anti-Ki-67 monoclonal antibody which is currently used for staining human esophageal cancer cells. Further, the malignant degree of esophageal cancer can be diagnosed according to the staining degree of esophageal cancer cells by anti-Mina53 monoclonal antibody.

The anti-Mina53 monoclonal antibody of the present invention can stain well cancer cells such as colon cancer, esophageal cancer, tongue cancer, breast cancer, sarcoma and brain tumor and the like, and then Mina53 can be used for diagnosing various cancers. On the other hand, the expression of Mina53 is inhibited to inhibit strongly the cell proliferation, and the application to cancer treatment is possible by suppressing Mina53 activity.

On the other hand, detection of Mina53 protein and mRNA encoding Mina53 in tissues and detection of abnormal cells such as cancer cells are useful for diagnosis. In such case, substances binding with Mina53 protein such as specific antibody like polyclonal antibody and monoclonal antibody and the like, or RNA or DNA having a sequence containing mina53 gene.

In the present invention, cell states can be measured by measuring the amount of expression of Mina53 contained in tissue sections according to ELIZA technique, Western blotting technique or the related techniques using substances binding with Mina53 protein such as polyclonal antibody and monoclonal antibody and the like. Further, cell states also can be diagnosed according to Northern blotting technique, RNase protection technique, RT-PCR method or cDNA micro-array technique and the like by using RNA or DNA having sequences containing mina53 gene. In the present invention, cancer cells can be diagnosed by measuring the amount of serum or urinary Mina53 protein.

Further, cancer can be diagnosed by estimating or measuring the existence and amount of abnormal cells such as cancer cells in the body according to techniques such as ELISA method widely adopted in the art by using antibody such as a polyclonal antibody and a monoclonal antibody against Mina53 protein.

Furthermore, the present invention has made the control of proliferation of abnormal cells such as cancer cells possible. In order to suppress Mina53 activity, for example, siRNA (small RNA interference RNA) technique, antisense nucleic acid method, transfection method of promoter-homologous nucleic acid, promoter-decoy method, ribozyme technique and the like can be employed and also substances binding with Mina53 (for example, protein such as antibody or lower molecular compounds and the like) can be used. The substances usable for Mina53 protein and nucleic acid sequence such as specific antibody or siRNA inhibiting the expression of mina53 and the methods such as screening for selecting the above-mentioned substances can also be used.

What is claimed is:

1. An agent for detecting a cancer, which comprises a monoclonal antibody that specifically binds to a peptide having an amino acid sequence designated by SEQ ID NO: 1 or a portion thereof, wherein the monoclonal antibody is produced by hybridoma FERM BP-10157.

2. A hybridoma producing the monoclonal antibody contained in the agent according to claim 1 which is FERM BP-10157.

3. The agent according to claim 1, further comprising a second antibody that specifically binds to the peptide or portion thereof of claim 1.

4. The agent according to claim 1, wherein the monoclonal antibody is immobilized on a support.

5. The agent according to claim 1, wherein the monoclonal antibody has a label.

* * * * *